United States Patent
Chen et al.

(10) Patent No.: US 11,542,337 B2
(45) Date of Patent: Jan. 3, 2023

(54) THERAPEUTIC IMMUNOGLOBULIN G4 FOR IMPROVED BIOANALYTICAL AND BIOPROCESSING PROPERTIES

(71) Applicant: BRISTOL-MYERS SQUIBB COMPANY, Princeton, NJ (US)

(72) Inventors: Zhiqiang Chen, Hudson, MA (US); Yueming Qian, Pepperell, MA (US); Xuankuo Xu, Boxborough, MA (US); Chao Huang, Shrewsbury, MA (US); Zhijun Tan, Acton, MA (US); Zhengjian Li, Sudbury, MA (US)

(73) Assignee: BRISTOL MYERS SQUIBB COMPANY, Princeton, NJ (US)

( * ) Notice: Subject to any disclaimer, the term of this patent is extended or adjusted under 35 U.S.C. 154(b) by 383 days.

(21) Appl. No.: 16/471,708

(22) PCT Filed: Dec. 22, 2017

(86) PCT No.: PCT/US2017/068154
§ 371 (c)(1),
(2) Date: Jun. 20, 2019

(87) PCT Pub. No.: WO2018/119380
PCT Pub. Date: Jun. 28, 2018

(65) Prior Publication Data
US 2020/0109208 A1   Apr. 9, 2020

Related U.S. Application Data

(60) Provisional application No. 62/438,684, filed on Dec. 23, 2016.

(51) Int. Cl.
| | | |
|---|---|---|
| C07K 16/28 | (2006.01) | |
| C07K 16/24 | (2006.01) | |
| C12N 15/13 | (2006.01) | |
| C07K 1/16 | (2006.01) | |
| C12N 15/62 | (2006.01) | |

(52) U.S. Cl.
CPC ............ *C07K 16/2878* (2013.01); *C07K 1/16* (2013.01); *C07K 16/24* (2013.01); *C07K 16/2818* (2013.01); *C07K 16/2827* (2013.01); *C07K 16/2866* (2013.01); *C12N 15/62* (2013.01); *C07K 2317/51* (2013.01); *C07K 2317/53* (2013.01); *C07K 2317/54* (2013.01); *C07K 2319/30* (2013.01)

(58) Field of Classification Search
None
See application file for complete search history.

(56) References Cited

U.S. PATENT DOCUMENTS

2009/0075338 A1   3/2009   Moore

FOREIGN PATENT DOCUMENTS

| WO | 2009041613 A1 | 4/2009 |
|---|---|---|
| WO | 2012022982 A2 | 2/2012 |
| WO | 2013124450 A1 | 8/2013 |
| WO | WO2016/026943 A1 | 2/2016 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Resaearch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
J. Schuurman, R. Van Ree, G.J. Perdok, H.R. Van Doorn, K.Y. Tan, R.C. Aalberse, Normal human immunoglobulin G4 is bispecific: it has two different antigen-combining sites, Immunology, 97 (1999) 693-698.
A.F. Labrijn, A.O. Buijsse, E.T. van den Bremer, A.Y. Verwilligen, W.K. Bleeker, S.J. Thorpe, J. Killestein, C.H. Polman, R.C. Aalberse, J. Schuurman, J.G. van de Winkel, P.W. Parren, Therapeutic IgG4 antibodies engage in Fab-arm exchange with endogenous human IgG4 in vivo, Nat Biotechnol, 27 (2009) 767-771.
A.M. Davies, B.J. Sutton, Human IgG4: a structural perspective, Immunological Reviews, 268 (2015) 139-159.
A.M. Davies, T. Rispens, T.H. den Bleker, J.M. McDonnell, H.J. Gould, R.C. Aalberse, B.J. Sutton, Crystal structure of the human IgG4 C(H)3 dimer reveals the role of Arg409 in the mechanism of Fab-arm exchange, Mol Immunol, 54 (2013) 1-7.
C. Wang, K.B. Thudium, M. Han, X.T. Wang, H. Huang, D. Feingersh, C. Garcia, Y. Wu, M. Kuhne, M. Srinivasan, S. Singh, S. Wong, N. Garner, H. Leblanc, R.T. Bunch, D. Blanset, M.J. Selby, A.J. Korman, In vitro characterization of the anti-PD-1 antibody nivolumab, BMS-936558, and in vivo toxicology in non-human primates, Cancer immunology research, 2 (2014) 846-856.
G. Scapin, X. Yang, W.W. Prosise, M. McCoy, P. Reichert, J.M. Johnston, R.S. Kashi, C. Strickland, Structure of full-length human anti-PD1 therapeutic IgG4 antibody pembrolizumab, Nature structural & molecular biology, 22 (2015) 953-958.
H. Luo, M. Cao, K. Newell, C. Afdahl, J. Wang, W.K. Wang, Y. Li, Double-peak elution profile of a monoclonal antibody in cation exchange chromatography is caused by histidine-protonation-based charge variants, J Chromatogr A, 1424 (2015) 92-101.

(Continued)

*Primary Examiner* — Joanne Hama
*Assistant Examiner* — Jon M Lockard

(57) ABSTRACT

In certain embodiments, the disclosure provides an IgG4 antibody comprising a heavy chain and a light chain, wherein the heavy chain comprises: (a) a modified IgG4 CH1 region having a substitution of the lysine residue at position 196; or (b) a modified IgG4 hinge region having a substitution of the serine residue at position 217, the glycine residue at position 220, the proline residue at position 224 or the proline residue at position 225. Preferably, the IgG4 antibody further comprises a substitution of the serine residue at position 228 in the heavy chain hinge region.

12 Claims, 22 Drawing Sheets

Specification includes a Sequence Listing.

(56) References Cited

OTHER PUBLICATIONS

J. Fu, J. Bongers, L. Tao, D. Huang, R. Ludwig, Y. Huang, Y. Qian, J. Basch, J. Goldstein, R. Krishnan, L. You, Z.J. Li, R.J. Russell, Characterization and identification of alanine to serine sequence variants in an IgG4 monoclonal antibody produced in mammalian cell lines, J Chromatogr B Analyt Technol Biomed Life Sci, 908 (2012) 1-8.

J. Guo, A.D. Creasy, G. Barker, G. Carta, Surface induced three-peak elution behavior of a monoclonal antibody during cation exchange chromatography, J Chromatogr A, 1474 (2016) 85-94.

J.G. Salfeld, Isotype selection in antibody engineering, Nat Biotech, 25 (2007) 1369-1372.

J.M. Reichert, Antibodies to watch in 2017, mAbs, 9 (2017) 167-181.

J.P. Silva, O. Vetterlein, J. Jose, S. Peters, H. Kirby, The S229P mutation prevents in vivo and in vitro IgG4 Fab-arm exchange as demonstrated using a combination of novel quantitative immunoassays and physiological matrix preparation, J Biol Chem, 290 (2015) 5462-5469.

J.S. van der Zee, P. van Swieten, R.C. Aalberse, Serologic aspects of IgG4 antibodies. II. IgG4 antibodies form small, nonprecipitating immune complexes due to functional monovalency, The Journal of Immunology, 137 (1986) 3566-3571.

J.W. Bloom, M.S. Madanat, D. Marriott, T. Wong, S.Y. Chan, Intrachain disulfide bond in the core hinge region of human IgG4, Protein science : a publication of the Protein Society, 6 (1997) 407-415.

M. van der Neut Kolfschoten, J. Schuurman, M. Losen, W.K. Bleeker, P. Martinez-Martinez, E. Vermeulen, T.H. den Bleker, L. Wiegman, T. Vink, L.A. Aarden, M.H. De Baets, J.G. van de Winkel, R.C. Aalberse, P.W. Parren, Anti-inflammatory activity of human IgG4 antibodies by dynamic Fab arm exchange, Science (New York, N.Y.), 317 (2007) 1554-1557.

S. Angal, D.J. King, M.W. Bodmer, A. Turner, A.D.G. Lawson, G. Roberts, B. Pedley, J.R. Adair, A single amino acid substitution abolishes the heterogeneity of chimeric mouse/human (IgG4) antibody, Molecular Immunology, 30 (1993) 105-108.

S. J. Peters et al: "Engineering an Improved IgG4 Moleculewith Reduced Disulfide Bond Heterogeneity and Increased FabDomain Thermal Stability",Journal of Biological Chemistryvol. 287, No. 29, Jul. 13, 2012 (Jul. 13, 2012), pp. 24525-24533.

T. Rispens, P. Ooijevaar-de Heer, O. Bende, R.C. Aalberse, Mechanism of immunoglobulin G4 Fab-arm exchange, J Am Chem Soc, 133 (2011) 10302-10311.

Y.M. Lucisano Valim, P.J. Lachmann, The effect of antibody isotype and antigenic epitope density on the complement-fixing activity of immune complexes: a systematic study using chimaeric anti-NIP antibodies with human Fc regions, Clinical and experimental immunology, 84 (1991) 1-8.

Kuo, et al., Journal of Chromatography A, Nov. 5, 2015, vol. 1424, p. 92-101.

\* cited by examiner

FIG. 11

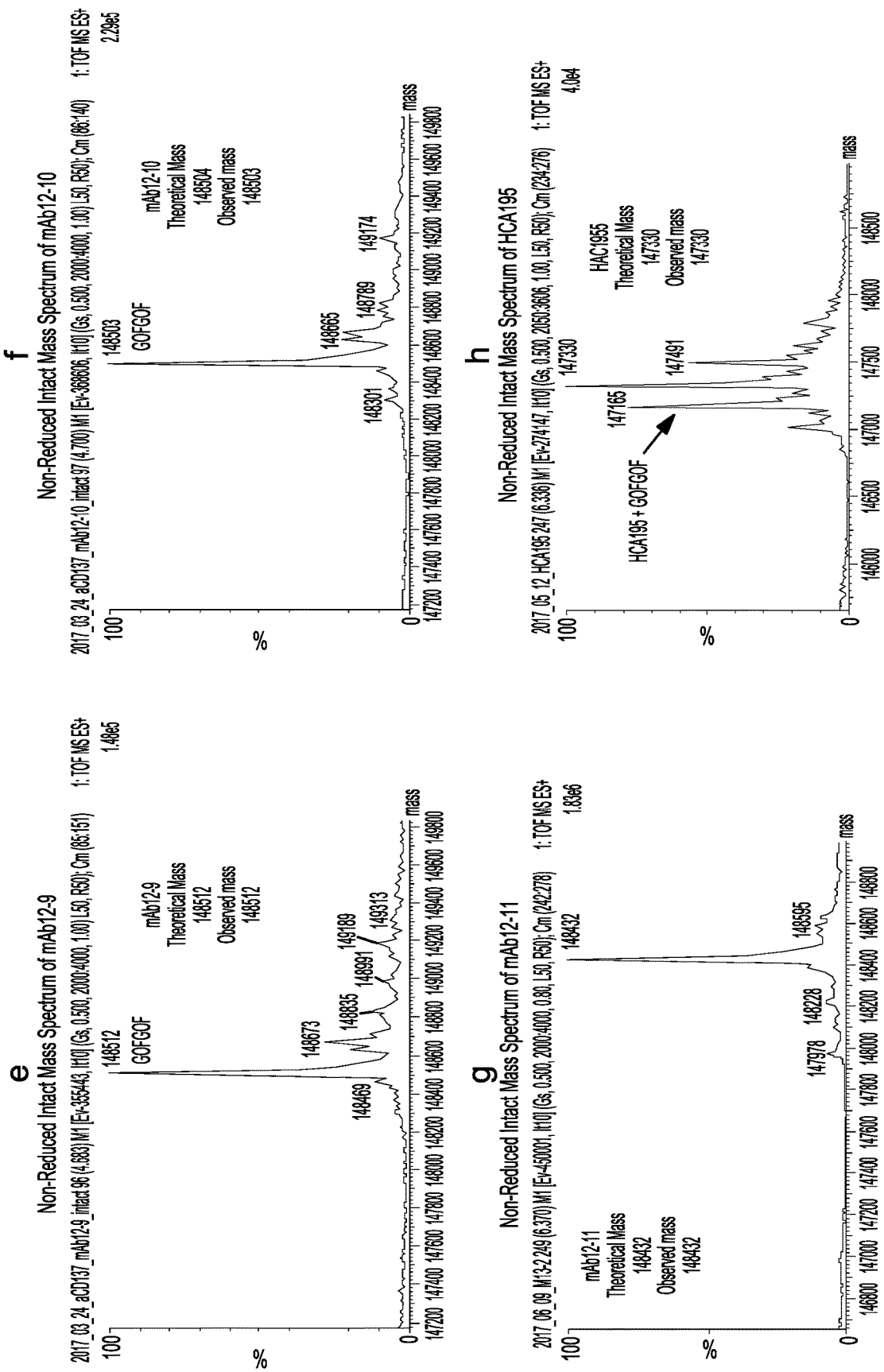
FIG. 13 (contd.)

SEQUENCE LISTING

```
<160> NUMBER OF SEQ ID NOS: 29

<210> SEQ ID NO 1
<211> LENGTH: 448
<212> TYPE: PRT
<213> ORGANISM: Artificial Sequence
<220> FEATURE:
<223> OTHER INFORMATION: Immunoglobulin Fragment Sequence

<400> SEQUENCE: 1
```

| | | | | | | | | | | | | | | | |
|---|---|---|---|---|---|---|---|---|---|---|---|---|---|---|---|
| Gln | Val | Gln | Leu | Gln | Gln | Trp | Gly | Ala | Gly | Leu | Leu | Lys | Pro | Ser | Glu |
| 1 | | | | 5 | | | | | 10 | | | | | 15 | |
| Thr | Leu | Ser | Leu | Thr | Cys | Ala | Val | Tyr | Gly | Gly | Ser | Phe | Ser | Gly | Tyr |
| | | | 20 | | | | | 25 | | | | | 30 | | |
| Tyr | Trp | Ser | Trp | Ile | Arg | Gln | Ser | Pro | Glu | Lys | Gly | Leu | Glu | Trp | Ile |
| | | | 35 | | | | | 40 | | | | | 45 | | |
| Gly | Glu | Ile | Asn | His | Gly | Gly | Tyr | Val | Thr | Tyr | Asn | Pro | Ser | Leu | Glu |
| | | 50 | | | | | 55 | | | | | 60 | | | |
| Ser | Arg | Val | Thr | Ile | Ser | Val | Asp | Thr | Ser | Lys | Asn | Gln | Phe | Ser | Leu |
| 65 | | | | | 70 | | | | | 75 | | | | | 80 |
| Lys | Leu | Ser | Ser | Val | Thr | Ala | Ala | Asp | Thr | Ala | Val | Tyr | Tyr | Cys | Ala |
| | | | | 85 | | | | | 90 | | | | | 95 | |
| Arg | Asp | Tyr | Gly | Pro | Gly | Asn | Tyr | Asp | Trp | Tyr | Phe | Asp | Leu | Trp | Gly |
| | | | 100 | | | | | 105 | | | | | 110 | | |
| Arg | Gly | Thr | Leu | Val | Thr | Val | Ser | Ser | Ala | Ser | Thr | Lys | Gly | Pro | Ser |
| | | | 115 | | | | | 120 | | | | | 125 | | |
| Val | Phe | Pro | Leu | Ala | Pro | Cys | Ser | Arg | Ser | Thr | Ser | Glu | Ser | Thr | Ala |
| | | | 130 | | | | | 135 | | | | | 140 | | |
| Ala | Leu | Gly | Cys | Leu | Val | Lys | Asp | Tyr | Phe | Pro | Glu | Pro | Val | Thr | Val |

-continued

```
              145                 150                 155                 160
        Ser Trp Asn Ser Gly Ala Leu Thr Ser Gly Val His Thr Phe Pro Ala
                            165                 170                 175

Val Leu Gln Ser Ser Gly Leu Tyr Ser Leu Ser Ser Val Val Thr Val
                            180                 185                 190

Pro Ser Ser Ser Leu Gly Thr Lys Thr Tyr Thr Cys Asn Val Asp His
                            195                 200                 205

Lys Pro Ser Asn Thr Lys Val Asp Lys Arg Val Glu Ser Lys Tyr Gly
                            210                 215                 220

Pro Pro Cys Pro Ser Cys Pro Ala Pro Glu Phe Leu Gly Gly Pro Ser
        225                 230                 235                 240

Val Phe Leu Phe Pro Pro Lys Pro Lys Asp Thr Leu Met Ile Ser Arg
                            245                 250                 255

Thr Pro Glu Val Thr Cys Val Val Val Asp Val Ser Gln Glu Asp Pro
                            260                 265                 270

Glu Val Gln Phe Asn Trp Tyr Val Asp Gly Val Glu Val His Asn Ala
                            275                 280                 285

Lys Thr Lys Pro Arg Glu Glu Gln Phe Asn Ser Thr Tyr Arg Val Val
                            290                 295                 300

Ser Val Leu Thr Val Leu His Gln Asp Trp Leu Asn Gly Lys Glu Tyr
        305                 310                 315                 320

Lys Cys Lys Val Ser Asn Lys Gly Leu Pro Ser Ser Ile Glu Lys Thr
                            325                 330                 335

Ile Ser Lys Ala Lys Gly Gln Pro Arg Glu Pro Gln Val Tyr Thr Leu
                            340                 345                 350

Pro Pro Ser Gln Glu Glu Met Thr Lys Asn Gln Val Ser Leu Thr Cys
                            355                 360                 365

Leu Val Lys Gly Phe Tyr Pro Ser Asp Ile Ala Val Glu Trp Glu Ser
                            370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Arg Leu Thr Val Asp Lys Ser
                            405                 410                 415

Arg Trp Gln Glu Gly Asn Val Phe Ser Cys Ser Val Met His Glu Ala
                            420                 425                 430

Leu His Asn His Tyr Thr Gln Lys Ser Leu Ser Leu Ser Leu Gly Lys
                            435                 440                 445

<210> SEQ ID NO 2
<211> LENGTH: 216
<212> TYPE: PRT
<213> ORGANISM: Artificial
<220> FEATURE:
<223> OTHER INFORMATION: Immunoglobulin Fragment Sequence

<400> SEQUENCE: 2

Glu Ile Val Leu Thr Gln Ser Pro Ala Thr Leu Ser Leu Ser Pro Gly
        1               5                   10                  15

Glu Arg Ala Thr Leu Ser Cys Arg Ala Ser Gln Ser Val Ser Ser Tyr
                    20                  25                  30

Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Gln Gln Arg Ser Asn Trp Pro Pro
                    85                  90                  95

Ala Leu Thr Phe Gly Gly Gly Thr Lys Val Glu Ile Lys Arg Thr Val
                    100                 105                 110

Ala Ala Pro Ser Val Phe Ile Phe Pro Pro Ser Asp Glu Gln Leu Lys
                    115                 120                 125

Ser Gly Thr Ala Ser Val Val Cys Leu Leu Asn Asn Phe Tyr Pro Arg
                    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                    165                 170                 175

Leu Ser Ser Thr Leu Thr Leu Ser Lys Ala Asp Tyr Glu Lys His Lys
                    180                 185                 190

Val Tyr Ala Cys Glu Val Thr His Gln Gly Leu Ser Ser Pro Val Thr
                    195                 200                 205

Lys Ser Phe Asn Arg Gly Glu Cys
210                 215

<210> SEQ ID NO 3
<211> LENGTH: 113
<212> TYPE: PRT
<213> ORGANISM: Artificial
<220> FEATURE:
<223> OTHER INFORMATION: Immunoglobulin Fragment Sequence

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                    35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                    100                 105                 110

Pro

<210> SEQ ID NO 4
<211> LENGTH: 113
<212> TYPE: PRT
<213> ORGANISM: Artificial
<220> FEATURE:
<223> OTHER INFORMATION: Immunoglobulin Fragment Sequence

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro

<210> SEQ ID NO 5
<211> LENGTH: 113
<212> TYPE: PRT
<213> ORGANISM: Artificial
<220> FEATURE:
<223> OTHER INFORMATION: Immunoglobulin Fragment Sequence

<400> SEQUENCE: 5

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro

<210> SEQ ID NO 6
<211> LENGTH: 113
<212> TYPE: PRT
<213> ORGANISM: Artificial
<220> FEATURE:
<223> OTHER INFORMATION: Immunoglobulin Fragment Sequence

<400> SEQUENCE: 6

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

Pro

<210> SEQ ID NO 7
<211> LENGTH: 113
<212> TYPE: PRT
<213> ORGANISM: Artificial
<220> FEATURE:
<223> OTHER INFORMATION: Immunoglobulin Fragment Sequence

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro

<210> SEQ ID NO 8
<211> LENGTH: 113
<212> TYPE: PRT
<213> ORGANISM: Artificial
<220> FEATURE:
<223> OTHER INFORMATION: Immunoglobulin Fragment Sequence

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro

<210> SEQ ID NO 9
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 10
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 11
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

```
Arg Val Glu Ser Lys Tyr Gly Pro Pro Cys Pro Pro Cys Pro
            100                 105                 110

<210> SEQ ID NO 12
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 13
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 14
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 14

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 15
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro
            100                 105                 110

<210> SEQ ID NO 16
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro
            100                 105                 110

<210> SEQ ID NO 17
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 17

Ala Ser Thr Lys Gly Pro Ser Val Phe Pro Leu Ala Pro Cys Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 18
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 18

Ala Ser Thr Lys Gly Pro Ser Val Phe Pro Leu Ala Pro Cys Ser Arg
1               5                   10                  15

Ser Thr Ser Gly Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 19
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 19

Ala Ser Thr Lys Gly Pro Ser Val Phe Pro Leu Ala Pro Cys Ser Arg
1               5                   10                  15

Ser Thr Ser Glu Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 20
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 20

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 21
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 21

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Arg Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 22

```
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Pro Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 23
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 23

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Ile Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 24
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Lys Thr
 65                  70                  75                  80

Tyr Thr Cys Asn Val Asn His Lys Pro Ser Asn Thr Lys Val Asp Lys
                    85                  90                  95

Arg Val Glu Ser Lys Tyr Gly Pro Pro Cys Pro Pro Cys Pro
                100                 105                 110

<210> SEQ ID NO 25
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 25

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                    85                  90                  95

Arg Val Glu Pro Lys Tyr Gly Pro Pro Cys Pro Pro Cys Pro
                100                 105                 110

<210> SEQ ID NO 26
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 26

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                    85                  90                  95

Arg Val Glu Ser Lys Lys Gly Pro Pro Cys Pro Pro Cys Pro
                100                 105                 110

<210> SEQ ID NO 27
<211> LENGTH: 110
<212> TYPE: PRT
<213> ORGANISM: Artificial

<220> FEATURE:
<223> OTHER INFORMATION: Immunoglobulin Fragment Sequence

<400> SEQUENCE: 27

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Thr Pro Pro Cys Pro Pro Cys Pro
            100                 105                 110
```

<210> SEQ ID NO 28
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 28

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly His Pro Cys Pro Pro Cys Pro
            100                 105                 110
```

<210> SEQ ID NO 29
<211> LENGTH: 110
<212> TYPE: PRT
<213> ORGANISM: Artificial
<220> FEATURE:
<223> OTHER INFORMATION: Immunoglobulin Fragment Sequence

<400> SEQUENCE: 29

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
-continued

Leu Ser Ser Val Val Thr Val Pro Ser Ser Ser Leu Gly Thr Lys Thr
 65              70                  75                  80

Tyr Thr Cys Asn Val Asp His Lys Pro Ser Asn Thr Lys Val Asp Lys
                 85                  90                  95

Arg Val Glu Ser Lys Tyr Gly Pro Thr Cys Pro Pro Cys Pro
            100                 105                 110
```

THERAPEUTIC IMMUNOGLOBULIN G4 FOR IMPROVED BIOANALYTICAL AND BIOPROCESSING PROPERTIES

REFERENCE TO RELATED APPLICATIONS

This application is a 371 application of PCT/US2017/068154, filed Dec. 22, 2017, which claims benefit to U.S. provisional patent application No. 62/438,684, Dec. 23, 2016, the contents of each of which are hereby incorporated herein by reference in their entirety.

BACKGROUND OF THE INVENTION

Monoclonal antibodies (mAbs) and their derivative products (e.g., Fc-fusion proteins) play an important role in treating some of the most challenging human diseases owing to the safety, efficacy and high quality of these types of biologics. The monoclonal antibody market is growing significantly fast, and it is estimated that the combined world-wide sales of monoclonal antibody products will reach approximately $125 billion by 2020. Immunoglobulin G (IgG) are among the most frequently used backbones for a therapeutic antibody. There are four subclasses, IgG1, IgG2, IgG3, and IgG4. IgG4 is the preferred subclass for the applications where recruitment of immune effector functions is not desired due the anti-inflammatory activities of IgG4 antibody.

Immunoglobulin G, isotype 4 (IgG4) are dynamic molecules that are able to exchange Fab arms by swapping a heavy chain and attached light chain (half molecule) with a heavy light chain pair from another molecule, resulting in bispecific antibodies. IgG4 Fab-arm exchange has been attributed to the IgG4 core-hinge sequence in conjunction with determinants in the CH3 domain. Therapeutic wild-type IgG4 was reported to exchange Fab arms with endogenous human IgG4, which may affect their therapeutic activity. To prevent Fab-arm exchange in vivo when designing therapeutic IgG4, serine 228 in the hinge area is often mutated to proline to generate therapeutic IgG4 (S228P under the EU numbering). Such mutations, however, can cause undesirable bioanalytical and bioprocessing behaviors.

Thus, there remains a need for design of therapeutic IgG4 molecules with improved bioanalytical and bioprocessing properties.

SUMMARY OF THE INVENTION

In certain embodiments, the disclosure provides an IgG4 antibody comprising a heavy chain and a light chain, wherein the heavy chain comprises: (a) a modified IgG4 CH1 region having a substitution of the lysine residue at position 196; or (b) a modified IgG4 hinge region having a substitution of the serine residue at position 217, the glycine residue at position 220, the proline residue at position 224 or the proline residue at position 225. Optionally, the IgG4 antibody further comprises a substitution of the serine residue at position 228 in the heavy chain hinge region. Preferably, the IgG4 antibody has improved bioanalytical or bioprocessing properties relative to a corresponding IgG4 molecule not comprising the substitution (also referred to an "unmodified IgG4 antibody" or "wild-type antibody"). For example, the serine residue at position 228 is changed to proline (S228P). To illustrate, the lysine residue at position 196 is changed to proline (K196P); the serine residue at position 217 is changed to proline (S217P); the glycine residue at position 220 is changed to threonine (G220T); the proline residue at position 224 is changed to histidine (P224H); the proline residue at position 225 is changed to threonine (P225T). Optionally, the IgG4 antibody is humanized or human. Optionally, the IgG4 antibody is a full-length antibody or an antibody fragment such as a F(ab)$_2$. In certain specific aspects, the IgG4 antibody binds to a target molecule selected from CD137, CXCR4, eTau, CSF1R, Lag3, PD1, PDL1 or KIR. For example, the IgG4 antibody comprises a substitution made in the heavy chain comprising the amino acid sequence of SEQ ID NO: 1. To illustrate, the IgG4 antibody comprises an amino acid sequence selected from SEQ ID NO: 22, 25, 27, 28, or 29. For example, the improved bioanalytical properties comprise a single-peak elution behavior on analytical cation exchange chromatography (CEX) rein, including but not limited to, ProPac SCX-10, Propac WCX-10, TSKgel® CM-5PW, TSKgel® BioAssist® S, TSKgel® SP-5PW, TSKgel® NPR, TSKgel® STAT, TSKgel® SP-2SW, SOURCE™ 15S 4.6/100 PE I, Mono S®, Discovery® BIO PolyMA-SCX, Antibodix® WCX-NP, Proteomix SCX-NP or Proteomix WCX-NP. To illustrate, the bioprocessing properties comprise a single-peak elution behavior on CEX resin, including but not limited to, Poros HS, Poros XS, carboxy-methyl-cellulose, BAKERBOND ABXTM, sulphopropyl immobilized on agarose and sulphonyl immobilized on agarose, MonoS, MiniS, Source 15S, 30S, SP sepharose, CM Sepharose, BAKERBOND Carboxy-Sulfon, WP CBX, WP Sulfonic, Hydrocell CM, Hydrocel SP, UNOsphere S, Macro-Prep High S, Macro-Prep CM, Ceramic HyperD S, Ceramic HyperD CM, Ceramic HyperD Z, Trisacryl M CM, Trisacryl LS CM, Trisacryl M SP, Trisacryl LS SP, Spherodex LS SP, DOWEX Fine Mesh Strong Acid Cation Resin, DOWEX MAC-3, Matrex Cellufine C500, Matrex Cellufine C200, Fractogel EMD SO3-, Fractogel EMD SE, Fractogel EMD COO—, Amberlite Weak and Strong Cation Exchangers, Diaion Weak and Strong Cation Exchangers, TSK Gel SP-5PW-HR, TSK Gel SP-5PW, Toyopearl CM (650S, 650M, 650C), Toyopearl SP (650S, 650M, 650C), CM (23, 32, 52), SE(52, 53), P11, Express-Ion C or Express-Ion S.

In certain embodiments, the present invention provides a fusion protein comprising: (a) a modified IgG4 heavy chain CH1 region having a substitution of the lysine residue at position 196; or (b) a modified IgG4 heavy chain hinge region having a substitution of the serine residue at position 217, the glycine residue at position 220, the proline residue at position 224 or the proline residue at position 225. Optionally, the IgG4 antibody comprises at least one mutation selected from K196P, S217P, G220T, P224H, or P225T. Optionally, the fusion protein further comprises a substitution of the serine residue at position 228 in the IgG4 heavy chain hinge region (e.g., the S228 mutation). Preferably, the fusion protein has improved bioanalytical and bioprocessing properties relative to an unmodified fusion protein (i.e., not comprising the amino acid modification at position 196, 217, 220, 224 or 225 of IgG4 heavy chain).

In certain embodiments, the present invention provides a method for improving bioanalytical or bioprocessing properties of an IgG4 antibody, said method comprising modifying the IgG4 antibody by substituting at least one residue at position 196, 217, 220, 224 or 225 of a human IgG4 heavy chain, wherein the modified IgG4 antibody has improved bioanalytical or bioprocessing properties relative to the unmodified IgG4 antibody. For example, the modified IgG4 antibody comprises at least one mutation selected from K196P, S217P, G220T, P224H, or P225T. Optionally, the IgG4 antibody comprises the S228P mutation. Optionally, the IgG4 antibody is humanized or human. Optionally, the IgG4 antibody is a full-length antibody or an antibody fragment such as a $F(ab)_2$. In certain specific aspects, the IgG4 antibody binds to a target molecule selected from CD137, CXCR4, eTau, CSF1R, Lag3, PD1, PDL1 or KIR. To illustrate, the improved bioanalytical properties comprise a single-peak elution behavior on analytical cation exchange chromatography (CEX) rein, including but not limited to, ProPac SCX-10, Propac WCX-10, TSKgel® CM-5PW, TSKgel® BioAssist® S, TSKgel® SP-5PW, TSKgel® NPR, TSKgel® STAT, TSKgel® SP-2SW, SOURCE™ 15S 4.6/100 PE I, Mono S®, Discovery® BIO PolyMA-SCX, Antibodix® WCX-NP, Proteomix SCX-NP or Proteomix WCX-NP. Optionally, the single peak elution behavior is used for the development of charge variant analysis method using CEX-HPLC for combination drugs. To illustrate, the bioprocessing properties comprise a single-peak elution behavior on CEX resin, including but not limited to, Poros HS, Poros XS, carboxy-methyl-cellulose, BAKERBOND ABXTM, sulphopropyl immobilized on agarose and sulphonyl immobilized on agarose, MonoS, MiniS, Source 15S, 30S, SP sepharose, CM Sepharose, BAKERBOND Carboxy-Sulfon, WP CBX, WP Sulfonic, Hydrocell CM, Hydrocel SP, UNOsphere S, Macro-Prep High S, Macro-Prep CM, Ceramic HyperD S, Ceramic HyperD CM, Ceramic HyperD Z, Trisacryl M CM, Trisacryl LS CM, Trisacryl M SP, Trisacryl LS SP, Spherodex LS SP, DOWEX Fine Mesh Strong Acid Cation Resin, DOWEX MAC-3, Matrex Cellufine C500, Matrex Cellufine C200, Fractogel EMD SO3-, Fractogel EMD SE, Fractogel EMD COO—, Amberlite Weak and Strong Cation Exchangers, Diaion Weak and Strong Cation Exchangers, TSK Gel SP-5PW-HR, TSK Gel SP-5PW, Toyopearl CM (650S, 650M, 650C), Toyopearl SP (650S, 650M, 650C), CM (23, 32, 52), SE(52, 53), P11, Express-Ion C or Express-Ion S.

In certain embodiments, the present invention provides a method for improving bioanalytical or bioprocessing properties of a fusion protein which comprises an IgG4 heavy chain CH1 or hinge region, said method comprising modifying the IgG4 heavy chain CH1 or hinge region by substituting at least one residue at position 196, 217, 220, 224 or 225 of the IgG4 heavy chain, wherein the modified fusion protein has improved bioanalytical or bioprocessing properties relative to the unmodified fusion protein. For example, the modified fusion protein comprises at least one mutation selected from K196P, S217P, G220T, P224H, or P225T. Optionally, the fusion protein comprises the S228P mutation. Preferably, the improved bioanalytical or bioprocessing properties comprise a single-peak elution behavior on cation exchange chromatography (CEX) rein.

In certain embodiments, the present invention provides a pharmaceutical composition comprising the IgG4 antibody or the fusion protein as described above; and (2) a pharmaceutically acceptable carrier. For example, the pharmaceutical composition is a liquid formulation. For example, the pharmaceutical composition is formulated for parenteral, subcutaneous, intravenous, intramuscular, intranasal, or pulmonary delivery. Optionally, the pharmaceutical composition further comprises another monoclonal antibody for combination therapy.

In certain embodiments, the present invention provides a nucleic acid comprising a nucleotide sequence encoding the IgG4 antibody or the fusion protein as described above.

In certain embodiments, the present invention provides a vector comprising a nucleotide sequence encoding the IgG4 antibody or the fusion protein as described above.

In certain embodiments, the present invention provides a host cell comprising a nucleotide acid encoding the IgG4 antibody or the fusion protein as described above (operably linked to a promoter). For example, the host cell is a mammalian cell.

In certain embodiments, the present invention provides a method of producing the IgG4 antibody or the fusion protein as described above, comprising culturing the a host cell comprising a nucleotide sequence encoding the IgG4 antibody or the fusion protein as described above under conditions appropriate for the expression of the IgG4 antibody or the fusion protein. Optionally, the method further comprises isolating the IgG4 antibody or the fusion protein. For example, the host cell is a mammalian cell.

In certain embodiments, the present invention provides a method of treating cancer in a subject (e.g., human), comprising administering to the subject a therapeutically effective amount of the IgG4 antibody or the fusion protein as described above.

In certain embodiments, the present invention provides a method of treating an autoimmune or inflammatory disease in a subject (e.g., human), comprising administering to the subject a therapeutically effective amount of the IgG4 antibody or the fusion protein as described above.

BRIEF DESCRIPTION OF THE DRAWINGS

FIG. 11 shows amino acid sequence alignment IgG4 (SERINE-TO-PROLINE (CPPC)) and IgG1 for constant heavy chain 1 (CH1) and hinge region. Total 12 amino acid differences are identified between IgG4 (SERINE-TO-PROLINE (CPPC)) and IgG1, and are highlighted with green and yellow. The first identified cysteine amino acid in IgG4 forms the inter-chain disulfide bond between heavy and light chain, thus cysteine was not mutated to corresponding serine to preserve IgG4 intact structure. The rest 11 amino acids in IgG4 (SERINE-TO-PROLINE (CPPC)) were mutated to corresponding amino acid individually in IgG1 to evaluate their impact on CEX-HPLC column behavior. Top panel shows partial sequences of mAb1 (SEQ ID NO: 3), mAb2 (SEQ ID NO: 4), mAb3 (SEQ ID NO: 5), mAb4 (SEQ ID NO: 6), mAb5 (SEQ ID NO: 7), mAb6 (SEQ ID NO: 8), mAb7 (SEQ ID NO: 9), mAb8 (SEQ ID NO: 10), mAb9 (SEQ ID NO: 11), mAb10 (SEQ ID NO: 12), mAb11 (SEQ ID NO: 13), mAb12 (SEQ ID NO: 14), mAb7-w (SEQ ID NO: 15), and mAb12-w (SEQ ID NO: 16). Bottom panel shows partial sequences of mAb12-1 (SEQ ID NO: 17), mAb12-2 (SEQ ID NO: 18), mAb12-3 (SEQ ID NO: 19), mAb12-4a (SEQ ID NO: 20), mAb12-4b (SEQ ID NO: 21), mAb12-4c (SEQ ID NO: 22), mAb12-5 (SEQ ID NO: 23), mAb12-6 (SEQ ID NO: 24), mAb12-7 (SEQ ID NO: 25), mAb12-8 (SEQ ID NO: 26), mAb12-9 (SEQ ID NO: 27), mAb12-10 (SEQ ID NO: 28), and mAb12-11 (SEQ ID NO: 29).

DETAILED DESCRIPTION OF THE INVENTION

Figure 1:
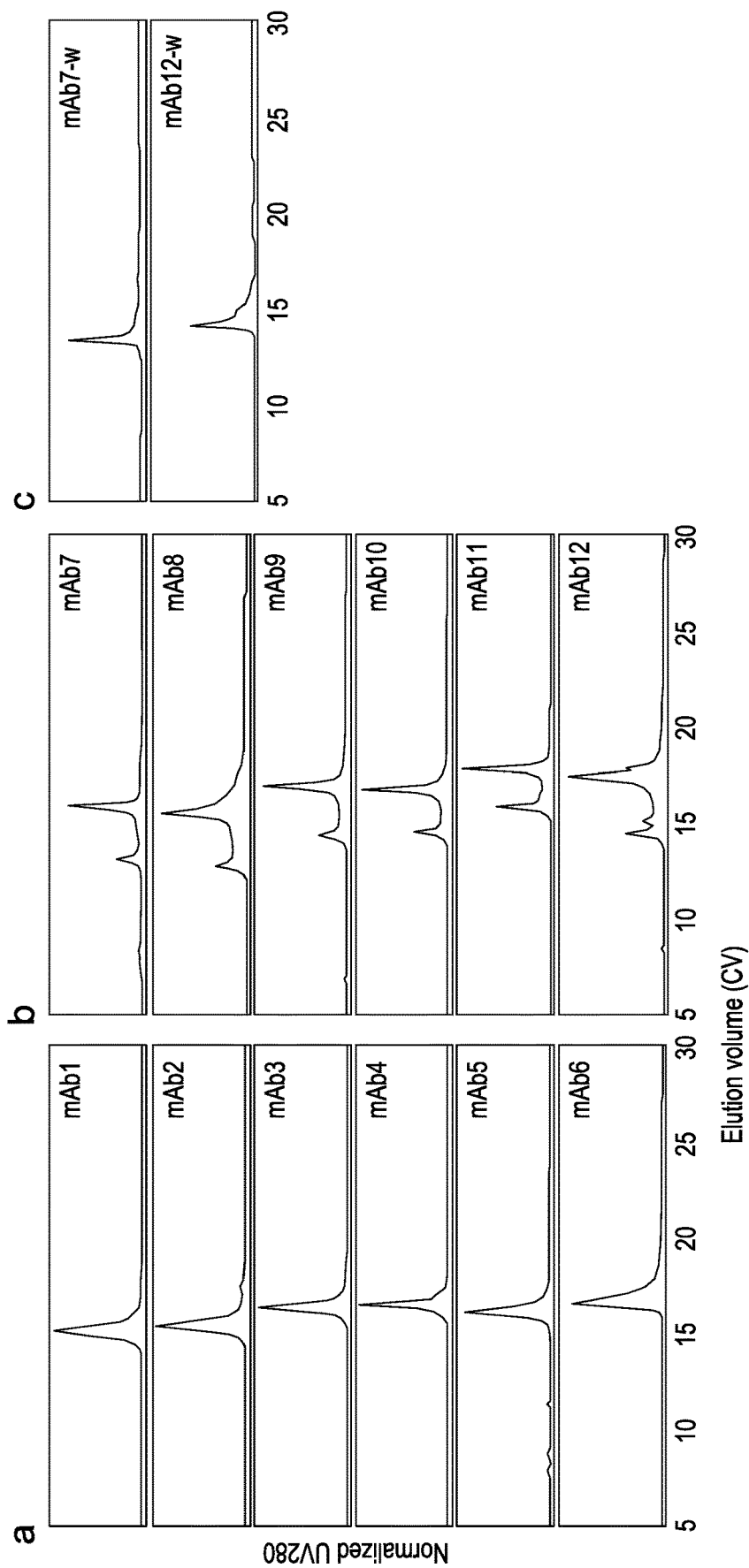
FIG. 1 shows CEX-HPLC chromatogram for therapeutic IgG4 molecules. Two-peak elution behaviors were observed on CEX-HPLC column for all therapeutic IgG4 molecules with the serine-to-proline (CPPC) mutation in the hinge. Single-peak elution behaviors were observed on CEX-HPLC column for all therapeutic IgG1 molecules and wild type IgG4. The CEX-HPLC method used salt gradient elution with 20 mM MES, pH 5.0 to 20 mM MES, 1 M NaCl, pH 5.0 (0-60 min) with a constant total injected protein mass of 10 μg.

In certain aspects, the present invention is based, at least in part, on the discovery that therapeutic IgG4 molecules with the S228P mutation (under the EU numbering) have undesirable bioanalytical and bioprocessing properties. To solve this problem, Applicants designed variant IgG4 molecules having improved bioanalytical and bioprocessing properties.

1. Definitions

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region. The heavy chain constant region typically is comprised of three domains, CH1, CH2, and CH3. Each light chain typically is comprised of a light chain variable region (abbreviated herein as $V_L$ or VL) and a light chain constant region. The light chain constant region typically is comprised of one domain, $C_L$ or CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)).

Often, the numbering of amino acid residues is performed by the method described in Kabat et al., Sequences of Proteins of Immunological Interest, 5th Ed. Public Health Service, National Institutes of Health, Bethesda, Md. (1991). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of VH CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

Alternatively, the numbering of amino acid residues is performed by the EU-index also described in Kabat et al., Sequences of Proteins of Immunological Interest, 5th Ed. Public Health Service, National Institutes of Health, Bethesda, Md. (1991). This numbering is used throughout this application.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions. The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. The term "antibody", unless specified otherwise, also includes polyclonal antibodies, monoclonal antibodies (mAbs), antibody-like polypeptides, such as chimeric antibodies, and humanized antibodies, bispecific antibodies, and antibody fragments retaining the ability to specifically bind to the antigen (antigen-binding fragments) provided by any known technique, such as enzymatic cleavage, peptide synthesis, and recombinant techniques. The constant region domains, in particular in the Fc domain, where present, are preferably of IgG4 isotype where antibody effector functions are not required. Accordingly, each heavy chain preferably comprises an IgG4 CH2 domain and a CH3 domain.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "chimeric antibody" refers to an antibody that contains one or more regions from one antibody and one or more regions from one or more other antibodies. The term "chimeric antibody" includes divalent and polyvalent antibodies. Chimeric antibodies are produced by recombinant processes well known in the art (see for instance Cabilly et al., PNAS USA 81, 3273-3277 (1984), Morrison et al., PNAS USA 81, 6851-6855 (1984), Boulianne et al., Nature 312, 643-646 (1984), EP125023, Neuberger et al., Nature 314, 268-270 (1985), EP171496, EP173494, WO86/01533, EP184187, Sahagan et al., J. Immunol. 137, 1066-1074 (1986), WO87/02671, Liu et al., PNAS USA 84, 3439-3443 (1987), Sun et al., PNAS USA 84, 214-218 (1987), Better et al., Science 240, 1041-1043 (1988) and Harlow et al., Antibodies: A Laboratory Manual, Cold Spring Harbor Laboratory Press, Cold Spring Harbor, N.Y., (1988)).

A "humanized antibody" is an antibody that is derived from a non-human species, in which certain amino acids in the framework and constant domains of the heavy and light chains have been mutated to avoid or abrogate an immune response in humans. Humanized forms of non-human (for instance murine) antibodies are chimeric antibodies which contain minimal sequence derived from non-human immunoglobulin. Generally, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody typically also will comprise at least a portion of an immunoglobulin constant region (Fc), typically that of a human immunoglobulin. For further details, see Jones et al., Nature 321, 522-525 (1986), Riechmann et al., Nature 332, 323-329 (1988) and Presta, Curr. Op. Struct. Biol. 2, 593-596 (1992).

An "isolated antibody" as used herein, is intended to refer to an antibody which is substantially free of other antibodies having different antigenic specificities. An isolated antibody that specifically binds to an epitope, isoform or variant of a particular human target antigen may, however, have cross-reactivity to other related antigens, for instance from other species (such as species homologs). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity, which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte.

As used herein, "isotype" refers to the immunoglobulin (sub)class, for instance IgG1, IgG2, IgG3, IgG4, IgD, IgA, IgE, or IgM, that is encoded by heavy chain constant region genes.

The term "bispecific antibody" is intended to include any antibody, which has two different binding specificities, e.g., the antibody binds two different epitopes, which may be located on the same target antigen or, more commonly, on different target antigens.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell, capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen or target cell. The expression of a particular FcR on an effector cell may be regulated by humoral factors such as cytokines.

The term "treatment" or "treating" refers to the administration of an effective amount of a therapeutically active molecule of the present invention with the purpose of easing, ameliorating, arresting or eradicating (curing) symptoms or disease states.

An "effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

The terms "Fab arm exchange" and "half-molecule exchange" are used interchangeably herein and refer to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules) while their Fc domain structure remains unchanged. Fab arm exchange occurs naturally in vivo and can be induced in vitro by purified blood cells or reducing agents such as reduced glutathione.

The terms "protein" and "polypeptide" are used interchangeably herein, unless the context indicates otherwise.

The terms "polynucleotide" includes a gene, DNA, cDNA, RNA, mRNA unless the context indicates otherwise.

The term "comprising" in context of the present specification should be interpreted as "including".

The term "wild-type" in the context of the present invention means an IgG4 molecule as it may occur in nature or may be isolated from the environment, which does not comprise any genetically engineered mutations.

2. Further Aspects and Embodiments of the Invention

In certain embodiments, the present invention provides a modified IgG4 molecule (also referred to as a modified IgG4 antibody or an antibody variant) or a modified fusion protein for use in the treatment of a disease. The present invention also provides a polynucleotide encoding the modified IgG4 antibody or fusion protein as well as a cell line expressing the modified IgG4 antibody or fusion protein. Further provided is a method for the treatment of a disease comprising administering a therapeutically effective amount of a modified IgG4 antibody or fusion protein.

In certain embodiments, the designation for a substitution mutant herein consists of a letter followed by a number followed by a letter. The first letter designates the amino acid in the wild-type protein. The number refers to the amino acid position where the amino acid substitution is being made, and the second letter designates the amino acid that is used to replace the wild-type amino acid. The residues in an antibody (e.g., an IgG4 molecule) variable and constant domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). The correct Kabat numbering of residues may be determined for a given antibody (e.g., an IgG4 molecule) by alignment of residues of homology in the sequence of the antibody with a "standard" Kabat numbered sequence. Alternatively, the numbering of amino acid residues may be performed by the EU-index or EU numbering system (also described in Kabat et al., Sequences of Proteins of Immunological Interest, 5th Ed. Public Health Service, National Institutes of Health, Bethesda, Md. (1991)). A further numbering system of amino acid residues in antibodies is the IMGT numbering system (Lefranc, M.-P. et al., Dev. Comp. Immunol., 29, 185-203 (2005)). In the present specification, the EU numbering system is used except where otherwise indicated that the Kabat numbering system is used.

Table 1 shows some exemplary modified IgG4 antibodies which comprise one or more mutations in the hinge or CH1 region.

TABLE 1

A representative list of mutations in an IgG4 molecule.

Figure 11:
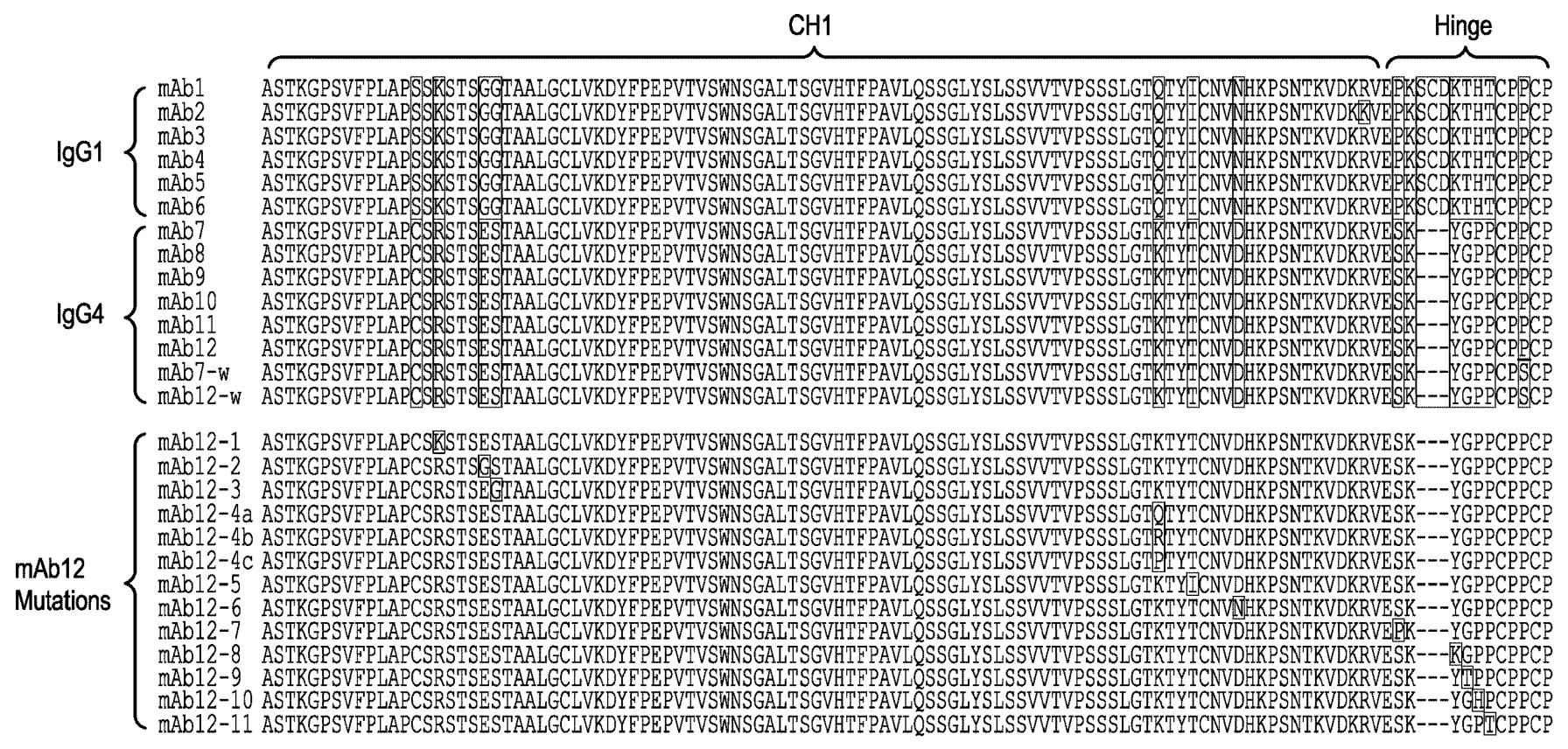

| Mutation location | Mutation numbering EU | Kabat | IgG4 antibodies comprising the mutation(s) |
|---|---|---|---|
| Hinge | S228P | S241P | mAb7-mAb12 and all mAb12 mutations listed in FIG. 11 |
| Hinge | S217P | S227P | mAb12-7 |
| Hinge | G220T | G230T | mAb12-9 |
| Hinge | P224H | P237H | mAb12-10 |
| Hinge | P225T | P238T | mAb12-11 |
| CH1 | K196P | K203P | mAb12-4c |

In certain embodiments, the disclosure provides an IgG4 antibody comprising a heavy chain and a light chain, wherein the heavy chain comprises: (a) a modified IgG4 CH1 region having a substitution of the lysine residue at position 196; or (b) a modified IgG4 hinge region having a substitution of the serine residue at position 217, the glycine residue at position 220, the proline residue at position 224 or the proline residue at position 225. Optionally, the IgG4 antibody further comprises a substitution of the serine residue at position 228 in the heavy chain hinge region. Preferably, the IgG4 antibody has improved bioanalytical or bioprocessing properties relative to a corresponding IgG4 molecule not comprising the substitution (also referred to an "unmodified IgG4 antibody" or "wild-type antibody"). For example, the serine residue at position 228 is changed to proline (S228P). To illustrate, the lysine residue at position 196 is changed to proline (K196P); the serine residue at position 217 is changed to proline (S217P); the glycine residue at position 220 is changed to threonine (G220T); the proline residue at position 224 is changed to histidine (P224H); the proline residue at position 225 is changed to threonine (P225T). Optionally, the IgG4 antibody is humanized or human. Optionally, the IgG4 antibody is a full-length antibody or an antibody fragment such as a F(ab)2. In certain specific aspects, the IgG4 antibody binds to a target molecule selected from CD137, CXCR4, eTau, CSF1R, Lag3, PD1, PDL1 or KIR. For example, the IgG4 antibody comprises a substitution made in the heavy chain comprising the amino acid sequence of SEQ ID NO: 1. To illustrate, the IgG4 antibody comprises an amino acid sequence selected from SEQ ID NO: 22, 25, 27, 28, or 29. For example, the improved bioanalytical properties comprise a single-peak elution behavior on analytical cation exchange chromatography (CEX) rein, including but not limited to, ProPac SCX-10, Propac WCX-10, TSKgel® CM-5PW, TSKgel® BioAssist® S, TSKgel® SP-5PW, TSKgel® NPR, TSKgel® STAT, TSKgel® SP-2SW, SOURCE™ 15S 4.6/100 PE I, Mono S®, Discovery® BIO PolyMA-SCX, Antibodix® WCX-NP, Proteomix SCX-NP or Proteomix WCX-NP. To illustrate, the bioprocessing properties comprise a single-peak elution behavior on CEX resin, including but not limited to, Poros HS, Poros XS, carboxy-methyl-cellulose, BAKERBOND ABXTM, sulphopropyl immobilized on agarose and sulphonyl immobilized on agarose, MonoS, MiniS, Source 15S, 30S, SP sepharose, CM Sepharose, BAKERBOND Carboxy-Sulfon, WP CBX, WP Sulfonic, Hydrocell CM, Hydrocel SP, UNOsphere S, Macro-Prep High S, Macro-Prep CM, Ceramic HyperD S, Ceramic HyperD CM, Ceramic HyperD Z, Trisacryl M CM, Trisacryl LS CM, Trisacryl M SP, Trisacryl LS SP, Spherodex LS SP, DOWEX Fine Mesh Strong Acid Cation Resin, DOWEX MAC-3, Matrex Cellufine C500, Matrex Cellufine C200, Fractogel EMD SO3-, Fractogel EMD SE, Fractogel EMD COO—, Amberlite Weak and Strong Cation Exchangers, Diaion Weak and Strong Cation Exchangers, TSK Gel SP-5PW-HR, TSK Gel SP-5PW, Toyopearl CM (650S, 650M, 650C), Toyopearl SP (650S, 650M, 650C), CM (23, 32, 52), SE(52, 53), P11, Express-Ion C or Express-Ion S.

In certain embodiments, the present invention provides a fusion protein comprising: (a) a modified IgG4 heavy chain CH1 region having a substitution of the lysine residue at position 196; or (b) a modified IgG4 heavy chain hinge region having a substitution of the serine residue at position 217, the glycine residue at position 220, the proline residue at position 224 or the proline residue at position 225. Optionally, the IgG4 antibody comprises at least one mutation selected from K196P, S217P, G220T, P224H, or P225T. Optionally, the fusion protein further comprises a substitution of the serine residue at position 228 in the IgG4 heavy chain hinge region (e.g., the S228 mutation). Preferably, the fusion protein has improved bioanalytical and bioprocessing properties relative to an unmodified fusion protein (i.e., not comprising the amino acid modification at position 196, 217, 220, 224 or 225 of IgG4 heavy chain).

In certain embodiments, the present invention provides a method for improving bioanalytical or bioprocessing properties of an IgG4 antibody, said method comprising modifying the IgG4 antibody by substituting at least one residue at position 196, 217, 220, 224 or 225 of a human IgG4 heavy chain, wherein the modified IgG4 antibody has improved bioanalytical or bioprocessing properties relative to the unmodified IgG4 antibody. For example, the modified IgG4 antibody comprises at least one mutation selected from K196P, S217P, G220T, P224H, or P225T. Optionally, the IgG4 antibody comprises the S228P mutation. Optionally, the IgG4 antibody is humanized or human. Optionally, the IgG4 antibody is a full-length antibody or an antibody fragment such as a F(ab)$_2$. In certain specific aspects, the IgG4 antibody binds to a target molecule selected from CD137, CXCR4, eTau, CSF1R, Lag3, PD1, PDL1 or KIR. To illustrate, the improved bioanalytical properties comprise a single-peak elution behavior on analytical cation exchange chromatography (CEX) rein, including but not limited to, ProPac SCX-10, Propac WCX-10, TSKgel® CM-5PW, TSKgel® BioAssist® S, TSKgel® SP-5PW, TSKgel® NPR, TSKgel® STAT, TSKgel® SP-2SW, SOURCE™ 15S 4.6/100 PE I, Mono S®, Discovery® BIO PolyMA-SCX, Antibodix® WCX-NP, Proteomix SCX-NP or Proteomix WCX-NP. Optionally, the single peak elution behavior is used for the development of charge variant analysis method using CEX-HPLC for combination drugs. To illustrate, the bioprocessing properties comprise a single-peak elution behavior on CEX resin, including but not limited to, Poros HS, Poros XS, carboxy-methyl-cellulose, BAKERBOND ABXTM, sulphopropyl immobilized on agarose and sulphonyl immobilized on agarose, MonoS, MiniS, Source 15S, 30S, SP sepharose, CM Sepharose, BAKERBOND Carboxy-Sulfon, WP CBX, WP Sulfonic, Hydrocell CM, Hydrocel SP, UNOsphere S, Macro-Prep High S, Macro-Prep CM, Ceramic HyperD S, Ceramic HyperD CM, Ceramic HyperD Z, Trisacryl M CM, Trisacryl LS CM, Trisacryl M SP, Trisacryl LS SP, Spherodex LS SP, DOWEX Fine Mesh Strong Acid Cation Resin, DOWEX MAC-3, Matrex Cellufine C500, Matrex Cellufine C200, Fractogel EMD SO3-, Fractogel EMD SE, Fractogel EMD COO—, Amberlite Weak and Strong Cation Exchangers, Diaion Weak and Strong Cation Exchangers, TSK Gel SP-5PW-HR, TSK Gel SP-5PW, Toyopearl CM (650S, 650M, 650C), Toyopearl SP (650S, 650M, 650C), CM (23, 32, 52), SE(52, 53), P11, Express-Ion C or Express-Ion S.

In certain embodiments, the present invention provides a method for improving bioanalytical or bioprocessing properties of a fusion protein which comprises an IgG4 heavy chain CH1 or hinge region, said method comprising modifying the IgG4 heavy chain CH1 or hinge region by substituting at least one residue at position 196, 217, 220, 224 or 225 of the IgG4 heavy chain, wherein the modified fusion protein has improved bioanalytical or bioprocessing properties relative to the unmodified fusion protein. For example, the modified fusion protein comprises at least one mutation selected from K196P, S217P, G220T, P224H, or P225T. Optionally, the fusion protein comprises the S228P mutation. Preferably, the improved bioanalytical or bioprocessing properties comprise a single-peak elution behavior on cation exchange chromatography (CEX) rein.

In certain embodiments, the present invention provides a pharmaceutical composition comprising the IgG4 antibody or the fusion protein as described above; and (2) a pharmaceutically acceptable carrier. For example, the pharmaceutical composition is a liquid formulation. For example, the pharmaceutical composition is formulated for parenteral, subcutaneous, intravenous, intramuscular, intranasal, or pulmonary delivery. Optionally, the pharmaceutical composition further comprises another monoclonal antibody for combination therapy.

In certain embodiments, the present invention provides a nucleic acid comprising a nucleotide sequence encoding the IgG4 antibody or the fusion protein as described above.

In certain embodiments, the present invention provides a vector comprising a nucleotide sequence encoding the IgG4 antibody or the fusion protein as described above.

In certain embodiments, the present invention provides a host cell comprising a nucleotide acid encoding the IgG4 antibody or the fusion protein as described above (operably linked to a promoter). For example, the host cell is a mammalian cell.

In certain embodiments, the present invention provides a method of producing the IgG4 antibody or the fusion protein as described above, comprising culturing the a host cell comprising a nucleotide sequence encoding the IgG4 antibody or the fusion protein as described above under conditions appropriate for the expression of the IgG4 antibody or the fusion protein. Optionally, the method further comprises isolating the IgG4 antibody or fusion protein. For example, the host cell is a mammalian cell.

3. Methods of Making Antibodies

Methods for the production of antibodies are well-known in the art. In a preferred embodiment, antibodies of the invention are monoclonal antibodies. Monoclonal antibodies may e.g., be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, or primates.

Further modifications, such as amino acid substitutions, deletions or insertion as described above, may be performed using standard recombinant DNA techniques well-known in the art.

In one embodiment, the antibody of the invention is a human antibody. Human monoclonal antibodies directed may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg, N. et al., Nature 368, 856-859 (1994)). Accordingly, the mice exhibit reduced expression of mouse IgM or $\kappa$ and in response to immunization, the introduced human heavy and light chain transgenes, undergo class switching and somatic mutation to generate high affinity human IgG,$\kappa$ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424).

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well known techniques. Such transgenic non-human animals, non-human animals comprising an operable nucleic acid sequence coding for expression of antibody used in the invention, non-human animals stably transfected with one or more target-encoding nucleic acid sequences, and the like, are additional features of the present invention.

Human monoclonal or polyclonal antibodies to be used in the present invention, or antibodies used in the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

Further, human or other antibodies to be used in the present invention may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Pluckthun, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hoogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

In a further aspect, the invention relates to a method for producing the modified antibody or fusion protein of the invention, said method comprising expressing a nucleic acid construct encoding said the modified antibody or fusion protein in a host cell and optionally purifying said the modified antibody or fusion protein.

In a further embodiment, the modified antibody or fusion protein of the invention is linked to a compound selected from the group consisting of: a cytotoxic agent; a radioisotope; a prodrug or drug, such as a taxane; a cytokine; and a chemokine. Methods for linking (conjugating) such compounds to an antibody are well-known in the art.

4. Pharmaceutic Compositions and Methods of Treatment

In a further aspect, the invention relates to a pharmaceutical composition comprising a modified antibody or fusion protein as defined herein above. The pharmaceutical compositions may be formulated with pharmaceutically acceptable carriers or diluents as well as any other known adjuvants and excipients in accordance with conventional techniques, such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) on antigen binding.

A pharmaceutical composition of the present invention may also include diluents, fillers, salts, buffers, detergents (e.g., a nonionic detergent, such as Tween-80), stabilizers, stabilizers (e.g., sugars or protein-free amino acids), preservatives, tissue fixatives, solubilizers, and/or other materials suitable for inclusion in a pharmaceutical composition.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. Optionally, administration is intravenous, intramuscular, intraperitoneal, by inhalation or subcutaneous. The effective daily dose of a therapeutic composition may be administered as two, three, four, five, six or more sub-doses administered separately at appropriate intervals throughout the day, optionally, in unit dosage forms.

In one embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

Modified antibody or fusion protein of the invention can be used in the treatment and/or prevention of a number of diseases, and be directed to any antigen selected from a broad variety of suitable target molecules. In one embodiment of the invention, the modified antibody or fusion protein of binds an antigen selected from the group consisting of erythropoietin, beta-amyloid, tau, thrombopoietin, interferon-alpha (2a and 2b), interferon-beta (1b), interferon-gamma, TNFR I (CD120a), TNFR II (CD120b), CD137, IL-1R type 1 (CD121a), IL-1R type 2 (CD121b), IL-2, IL2R (CD25), IL-2R-beta (CD123), IL-3, IL-4, IL-3R (CD123), IL-4R (CD124), IL-5R (CD125), IL-6R-alpha (CD126), -beta (CD130), IL-8, IL-10, IL-11, IL-15, IL-15BP, IL-15R, IL-20, IL-21, TCR variable chain, RANK, RANK-L, CTLA4, CXCR4, CXCR4R, CCR5R, TGF-beta1, -beta2, -beta3, G-CSF, GM-CSF, MIF-R (CD74), M-CSF-R (CD115), GM-CSFR (CD116), soluble FcRI, sFcRII, sFcRIII, FcRn, Factor VII, Factor VIII, Factor IX, VEGF, alpha-4 integrin, Cd11a, CD18, CD20, CD38, CD25, CD74, FcαRI, FcεRI, acetyl choline receptor, fas, fasL, TRAIL, hepatitis virus, hepatitis C virus, envelope E2 of hepatitis C virus, tissue factor, a complex of tissue factor and Factor VII, EGFr, CD4, CD28, VLA-1, 2, 3, or 4, LFA-1, MAC-1, 1-selectin, PSGL-1, ICAM-I, P-selectin, periostin, CD33 (Siglec 3), Siglec 8, TNF, CCL1, CCL2, CCL3, CCL4, CCL5, CCL11, CCL13, CCL17, CCL18, CCL20, CCL22, CCL26, CCL27, CX3CL1, EGF, VEGF, TGFalpha, HGF, PDGF, NGF, CD32b, CD200, CD200R, Killer Immunoglobulin-Like Receptors (KIRs), NKG2D, leukocyte-associated immunoglobulin-like receptors (LAIRs), Iy49, PD-L1, PD-L2, CD26, BST-2, ML-IAP (melanoma inhibitor of apoptosis protein), cathepsin D, CD40, CD40R, CD86, a B cell receptor, CD79, PD-1, Lag3, and a T cell receptor.

In certain specific aspects, the modified IgG4 antibody or fusion protein binds to a target molecule selected from CD137, CXCR4, eTau, CSF1R, Lag3, PD1, PDL1 or KIR.

In another specific embodiment, the modified antibody or fusion protein of the present invention is for use in the treatment of malignant diseases and/or metastising diseases, such as melanoma, ovary cancer, endometrial cancer, NSCLC, glioblastoma, brain-related tumors, breast cancer, OSCC, colon cancer, renal cancer, pancreatic cancer, HNSCC, kidney cancer, thymoma, lung cancer, skin cancer, larynx cancer, liver cancer, parotid tumors, gastric cancer, esophagus cancer, prostate cancer, bladder cancer, cancer of the testis, leukemia, and lymphoma.

In one specific embodiment, the modified antibody or fusion protein of the present invention is for use in the treatment of inflammatory and autoimmune diseases, such as rheumatoid arthritis, multiple sclerosis, inflammatory bowel disease, asthma, type-1 diabetes, SLE, psoriasis, atopic dermatitis, graft-versus-host disease (GVHD), and COPD.

The present invention is further illustrated by the following examples which should not be construed as further limiting. The contents of all figures and all references, patents and published patent applications cited throughout this application are expressly incorporated herein by reference.

EXAMPLES

Example 1

Design of Therapeutic IgG4 for Improved Bioanalytical and Bioprocessing Properties
I. Introduction Therapeutic IgG4 antibodies are engineered in the hinge region to have the Cys-Pro-Pro-Cys (CPPC) motif to prevent Fab-arm exchange [10, 15, 16]. However, the serine-to-proline substitution in the core-hinge region of therapeutic IgG4 challenges robust chemistry, manufacturing, and control (CMC) development. Two-peak elution behavior is observed on cation exchange chromatography (CEX) for all therapeutic IgG4 antibodies with CPPC modification, creating hurdles to bioanalytical method development and bioprocessing development for robust manufacturing. Here, we present the design of next generation therapeutic IgG4 antibodies with single point mutation in the CH1 domain or hinge region for improved bioanalytical and bioprocessing properties by combining protein engineering and mutagenesis. Molecular modelling and simulation suggested that significant secondary structure and/or hinge region flexibility change can occur even for single point mutation in IgG4, which may lead to unexpected CMC behaviors. Thus, the CMC behavior should be carefully considered when designing therapeutic IgG4 antibodies as well as other IgG isotypes.

Immunoglobulin G (IgG) is the most frequently used backbone for therapeutic antibody development, and is subdivided into four subclasses: IgG1, IgG2, IgG3, and IgG4. Among the IgG isotypes, IgG4 is the preferred subclass for the applications where recruitment of immune effector functions is not desired due to its incapability of activating the classical complement pathway [1]. IgG4 behaves differently from other IgG isotypes in its inability to cross-link two identical antigens in plasma, which is also known as functionally monovalent [2]. In vivo study unveiled that IgG4 is able to cross-link two different antigens to form bispecific antibodies [3] by swapping a heavy chain and attached light chain (half molecule) with a heavy light chain pair from another molecule, known as Fab-arm exchange [4]. Fab-arm exchange can be a major disadvantage for IgG4 human immunotherapy due to the unpredictability of the Fab-arm combinations. Exchanging between therapeutic IgG4 and endogenous human IgG4 in vivo results in bispecific antibodies with unknown and undesirable specificity. The formation of functionally monovalent bispecific antibodies changes therapeutic IgG4's ability to cross-link the originally targeted antigen, which can affect the pharmacokinetics and efficacy as well as pharmacodynamics for human immunotherapy [5].

Fab-arm exchange has been attributed to two distinctive structural features of IgG4: Cys-Pro-Ser-Cys (CPSC) motif in the core-hinge region and R409 amino acid in the CH3 domain [4, 6]. R409 and K409 are the primary interface between the two CH3 domains for IgG4 and IgG1 respectively. Unlike the strong non-covalent interaction between CH3 domains in IgG1 with K409 residue, the CH3-CH3 interaction is much weaker for IgG4, as R409 prevents the proper formation of an inter-chain hydrogen bond network [7], thereby allowing dissociation and predisposing IgG4 to the Fab-arm exchange [8]. Mutation of R409K in the CH3 domain of IgG4 help stabilize the antibody. CPPC and CPSC motif in the core-hinge region is another major difference between IgG1 and IgG4. The relative rigidity induced by the proline from the CPPC motif in IgG1 hampers the formation of intrachain disulfide bonds [9]. Differently, the CPSC motif in IgG4 allows for more hinge flexibility and the ability to adopt an intrachain disulfide bonds. As a result, noncovalently associated half molecules are formed as evidenced by non-reducing SDS-PAGE [9, 10], which then will interact with other half molecules to form bispecific antibodies. To address this problem, serine-to-proline substitution was introduced to make the hinge region more like that found in IgG1 [10]. The modified IgG4 hinge with CPPC motif is more stable and avoid the Fab-arm exchange with endogenous human IgG4 in vivo. Nivolumab and pembrolizumab, two recently FDA approved anti-PD-1 (programmed death-1) IgG4 cancer therapeutics, both contain the modified hinge with CPPC motif [11-13]. Furthermore, a number of other IgG4 antibodies, with serine-to-proline substitutions in the hinge region, are currently in preclinical or clinical trials [14]. It is being accepted that the simple serine-to-proline mutation (CPPC) can prevent in vivo fab-arm exchange without rising any risks or challenges for therapeutic IgG4. Such mutations, however, can cause undesirable bioanalytical and bioprocessing behaviors. Thus, there remains a need for design of therapeutic IgG4 molecules with improved bioanalytical and bioprocessing properties.

II. Materials and Methods

1. CEX-HPLC Method

Analytical CEX-HPLC was carried out using a ProPac SCX-10 LC Columns column from Thermo Fisher Scientific (Wilmington, Del., USA) installed on a Waters HPLC system from Waters Corporation (Milford, Mass., USA). The method used salt gradient elution with 20 mM MES, pH 5.0 to 20 mM MES, 1 M or 0.6 M NaCl, pH 5.0 (0-60 min) with a constant total injected protein mass of 10 µg. The eluted protein was monitored by UV 280 nm.

2. SEC Method for Aggregate Analysis

Analytical SEC was carried out using a TSKgel G3000SWXL column from Tosoh Bioscience (King of Prussia, Pa., USA) installed on a Waters HPLC system from Waters Corporation (Milford, Mass., USA). The method used 100 mM sodium phosphate, 100 mM sodium sulfate, pH 6.8, at a flow rate of 1 mL/min, with a constant total injected protein mass of 100 µg. The eluted protein was monitored by UV 280 nm.

3. Chromatography Instrumentation and Methods

All chromatography runs were performed using a GE Healthcare ÄKTA AVANT system installed with Unicorn software version 6.3 (Piscataway, N.Y., USA). Poros XS resins were packed into omnifit columns (0.66 cm I.D×10 cm bed height) purchased from Fisher Scientific (Hampton, N.H. USA). The packed and conditioned column was equilibrated with 5 column volumes (CV) of 25 mM MES buffer, pH 5.0. The CEX column was loaded at 1 g/L resin at pH 5, followed by a 30 CV 0-1 M NaCl gradient in 20 mM MES buffer at pH 5. The column was regenerated with 3 CV of 1M NaCl, sanitized with 3 CV of 1 M NaOH, and finally stored in 0.1 M NaOH after each run. Protein concentration was measured using a NanoDrop 2000 purchased from Thermo Fisher Scientific (Wilmington, Del., USA). All runs were performed at room temperature.

4. ICE280 Method

Imaged capillary isoelectric focusing (iCIEF) was performed using an iCE280 Analyzer (Convergent Bioscience, Toronto, Canada) to examine charge variants. The separation cartridge along with capillary was purchased from Convergent Bioscience. This capillary was fixed onto a glass substrate and separated from the catholyte and anolyte by two pieces of hollow fiber membrane. An IgG sample was prepared by mixing 2 mg/mL IgG with various pI markers, 1% methyl cellulose solution, and pharmalyte 3-10, before diluted with deionized water. The mixture was centrifuged and supernatant was focused in station for varied lengths of time to achieve the optimum resolution. The final image of the IEF trace was captured by the 280 nm deuterium lamp detector.

5. Preparation of F(ab')$_2$ Domain of Anti-CD137 (S228P) Using Pepsin Digestion The agarose immobilized pepsin was purchased from Thermo scientific (Waltham, Mass., USA). Anti-CD137 (S228P) was digested by pepsin-agarose (0.25 mL pepsin-agarose per 20 mg anti-CD137 (S228P)) at pH 4.5 in a 37° C. water bath for 4 hr. The digested product was adjusted to pH 7.0 and then was purified by flowing through a MabSelect Sure column pre-equilibrated at pH 7.0. The small Fc fragments were washed away during 10 mM Tris.HCl wash, and the F(ab')$_2$ domain was collected during 25 mM phosphate buffer wash, the undigested mAb and Fc domains were retained on the MabSelect Sure column.

6. Preparation of F(ab) Domain of Anti-CD137 (S228P) Using Papain Digestion

The agarose immobilized papain was purchased from Thermo scientific (Waltham, Mass., USA). Anti-CD137 (S228P) was digested by papain-agarose in 20 mM sodium phosphate, 20 mM cysteine.HCl, 10 mM EDTA; pH 7.0 (0.25 mL papain agarose per 10 mg anti-CD137 (S228P)) at pH 7 in a 37° C. water bath for 4 hr. The Fab fragments was separated from undigested mAb and Fc fragments using an immobilized Protein A column.

7. Cell Lines and Culture Condition

ExpiCHO-S cells (ThermoFisher Scientific) were grown in defined and serum-free ExpiCHO expression medium (ThermoFisher Scientific) and passaged in shake flasks every three days. Cells were incubated at 130 rpm on an orbital shaker platform in a 37° C. incubator with a humidified atmosphere of 8% $CO_2$.

8. Construction of IgG4-anti-CD137 Mutants

Site-directed mutagenesis was carried out with single amino acid substitutions in CH1 and hinge regions. The template DNA of IgG4-anti-CD137 plasmid was methylated prior to the mutagenesis reaction, in which two overlapping primers were used and one of them contained the target mutation. The mutagenesis products were transformed into E. coli competent cells, where unmethylated linear mutated DNA was circularized and replicated. Plasmid DNAs were isolated and purified with a PureLink Hi Pure Plasmid Maxiprep kit (ThermoFisher Scientific).

9. Transient Expression of Anti-CD137 and its Variants in ExpiCHO-S Suspension Cells One day prior to transfection, cells were seeded at 3.0 million cells/ml and agitated on an orbital shaker platform rotating at 130 rpm at 37° C. with 8% $CO_2$. On the day of transfection (Day-0), cells were diluted to 6.0 million cells/ml and added into a 250-ml shake flask at 50 ml culture volume. Fifty micrograms of plasmid DNA were diluted into Opti-Pro SFM (ThermoFisher Scientific) to a total volume of 2.0 ml and mixed. In a separate tube, 160 µl of Expi-Fectamine CHO Reagent (ThermoFisher Scientific) was also diluted with Opti-Pro SFM to a total volume of 2.0 ml. Diluted DNA solution and diluted transfection reagent were mixed gently and incubated at room temperature for 5 minutes. DNA-transfection-reagent mixture was then slowly added to freshly diluted cells in 250-ml flasks. Transfected cells were incubated at 37° C., 8% $CO_2$ on an orbital shaker platform rotating at 130 rpm. On day-1, the culture was fed with 10 ml of ExpiCHO Feed (ThermoFisher Scientific) and 300 µl of ExpiCHO Enhancer (ThermoFisher Scientific); the incubation temperature and $CO_2$ were shifted to 32° C. and 5%, respectively. The culture received the second bolus of the feed on day-6 and was harvested on day-13. Both anti-CD137 and its mutants were robustly expressed in ExpiCHO-S transient expression system, indicating that amino acid replacements in the target regions did not impact IgG4 synthesis.

10. Anti-CD137 Binding Assay

The assay plates were coated with 100 μL (2 μg/mL) of Human CD137 Murine IgGb2 in bicarbonate buffer for 1 hr at room temperature. The plates were then blocked with 300 μL of SeaBlock solution (Pierce #37527) for 1 hr at room temperature. Reference material and the samples were diluted to 1 μg/mL in Teknova assay diluent buffer (Teknova-#D5120) followed by 2 fold serial dilutions.

The blocking buffer was decanted and plate washed three times with 300 μL of Wash buffer (PBS-T). The samples and reference standards (100 μL) were added to the plate and incubated for 1 hr at room temperature. After 3 washes the 100 μL of Secondary Antibody (anti-Human IgG4 Fc, HRP; 1:1000 in Teknova diluent) was added and incubated for 1 hr at room temperature.

After washing, 100 μL of Dako TMB was added and incubated for 10 minutes. The reaction was stopped with 100 μL of 1N sulfuric acid. The absorbance was readapt 450 nm with 650 nm as background correction using Softmax software on M5 plate reader (Molecular Devices). The EC50 values were calculated from the absorbance values vs. log concentrations of samples and reference at each dilution. The percent relative binding potency was calculated by dividing the reference material EC50 by the test sample EC50 as a percentage.

11. Intact Mass Analysis

The LC-MS was performed with an Acquity UHPLC coupled with a quadrupole time-of-flight (Q-ToF) mass spectrometer (Waters, Milford, Mass.). The capillary voltage for the Q-ToF was set at 3000 V and the sample cone voltage at 80 V. The method for analysis was the same as described previously.[17] In brief, purified samples were incubated with 5 mM DTT at 37° C. for 20 mins for reduction, which was stopped by adding formic acid to a final concentration of 0.2% (v:v). The reduced sample was injected at 0.5 μg onto a reversed phase (RP) column (10 μm, 2.1×100 mm Poros®, Applied Biosystems, Foster City, Calif.) equilibrated with 20% acetonitrile containing 0.1% formic acid, followed by gradient elution from 20% to 50% acetonitrile in 25 min, at a flow rate of 0.25 mL/min. The mass spectra were scanned from m/z 500 to 4000; the combined data were then deconvoluted using MaxEnt1 algorithm (Waters, Milford, Mass.).

Fab-arm exchange conditions: mAb12 mutation was mixed with HCA195 and incubated with 0.5 mM reduced glutathione (GSH; Sigma) in degassed PBS (pH7.2). The final concentration of both mAb12 mutation and HCA195 was 20 μg/mM. The mixtures (70 μL) were incubated at 37 degree for 24 h. The samples were then stored at 4 degree before intact mass testing [4].

III. Results and Discussion

We report here that the SERINE-TO-PROLINE (CPPC) mutation in the hinge region, however, causes tremendous challenge for various IgG4 CMC development (see Table 2).

TABLE 2

A list of antibodies and their isotypes

| mAb symbol | isotype | Antibody |
|---|---|---|
| mAb0 | IgG1 | |
| mAb1 | IgG1 | |
| mAb2 | IgG1 | |
| mAb3 | IgG1 | |
| mAb4 | IgG1 | |
| mAb5 | IgG1 | |
| mAb6 | IgG1 | |
| mAb7 | IgG4 | HCA247 (bio-rad) |
| mAb7-w | IgG4 | HCA195 (bio-rad) |
| mAb8 | IgG4 | anti-CSF1R |
| mAb9 | IgG4 | anti-lag3 |
| mAb10 | IgG4 | Nivolumab |
| mAb11 | IgG4 | anti-CXCR4 |
| mAb12 | IgG4 | anti-CD137 |
| mAb13 | Fc-fusion protein with IgG4 hinge | anti-CD40 |

Two-peak elution behaviors on analytical CEX column were observed for all therapeutic IgG4 with CPPC motif modification mutation (FIG. 1b), while single-peak elution behaviors was observed for all IgG1 and wild-type IgG4 (mAb7-w, and mAb12-2) (FIGS. 1a, c). Two-peak elution behavior on CEX column was also previously reported by other studies, and was either attributed to a specific molecule [18] or a specific resin[19]. Luo et al [18] reported the two-peak elution behavior on CEX for an IgG4 with histidine residue surrounded by 4 hydrophobic residues in primary structure in the complementary determining (CDR) regions, and linked it to the separation of histidine-protonation-based charge variants in the CDR. However, our antibody sequence analysis indicated that mAb8, mAb9, mAb11 and mAb12 do not contain a similar histidine residue in the CDR but show two-peak elution behavior; mAb4 and mAb6 does contain a similar histidine residue in the CDR but show single-peak elution behavior. Guo et al [19] reported surface induced three-peak elution behavior of a monoclonal antibody on Poros XS resin, and concluded that bi-modal pore size distribution of poros XS resin induced two binding sites for the protein thus are responsible for the two peaks behavior. However, two-peak elution behavior were also observed on non-porous resin Propac SCX-10 resin for all mutated IgG4 molecules used in our study. The only difference between mutated IgG4 and wild-type IgG4 is the CPPC and CPSC motif in the hinge region. Apparently, the SERINE-TO-PROLINE (CPPC) mutation in the hinge region caused these two-peak elution behaviors on CEX column.

Figure 2:
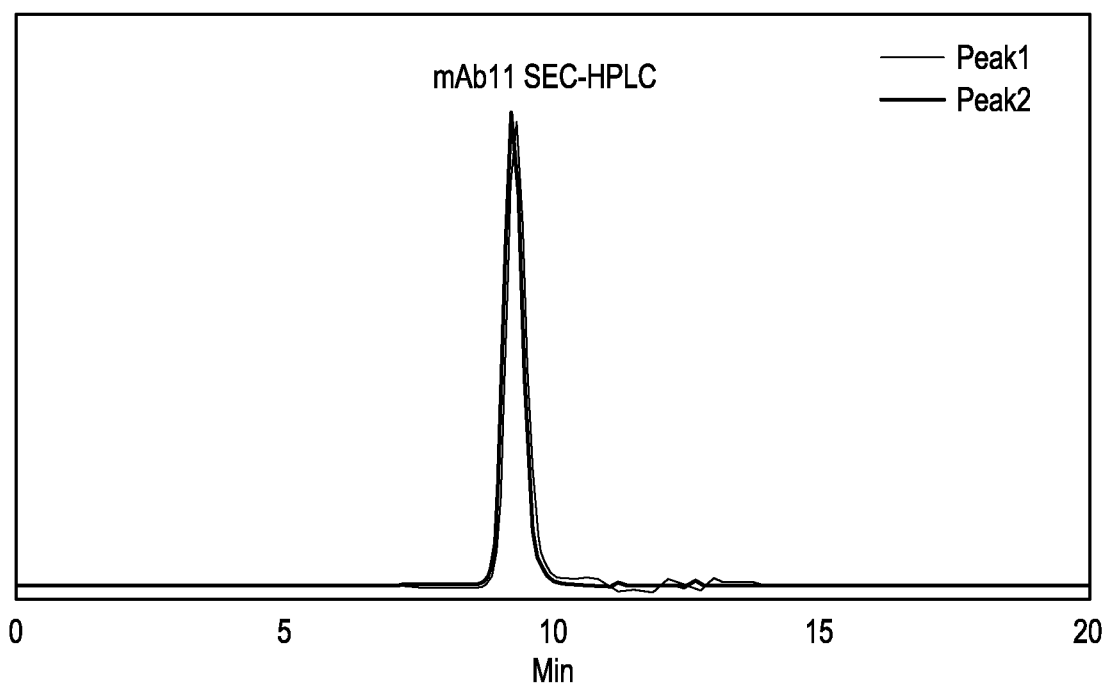
FIG. 2 shows SEC-HPLC chromatogram for mAb11, peak 1 and peak 2 of CEX-HPLC. The two chromatograms overlaid very well, indicating no size difference or aggregation formation for the two peaks. Analytical SEC was carried out using a TSKgel G3000SWXL column from Tosoh Bioscience (King of Prussia, Pa., USA) installed on a Waters HPLC system from Waters Corporation (Milford, Mass., USA). The method used 100 mM sodium phosphate, 100 mM sodium sulfate, pH 6.8, at a flow rate of 1 mL/min, with a constant total injected protein mass of 100 μg. The eluted protein was monitored by UV 280 nm.
Figure 3:
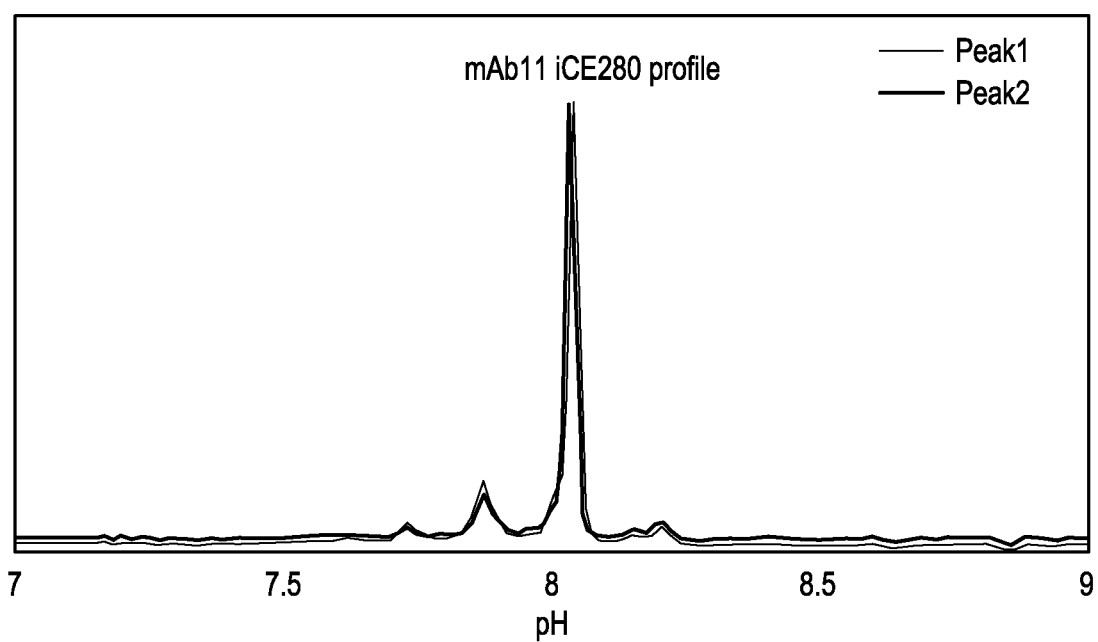
FIG. 3 shows iCE280 profile for peak 1 and peak 2 formed on CEX-HPLC for therapeutic mAb11. The two chromatograms overlaid very well, indicating no charge difference for these two peaks.
Figure 4:
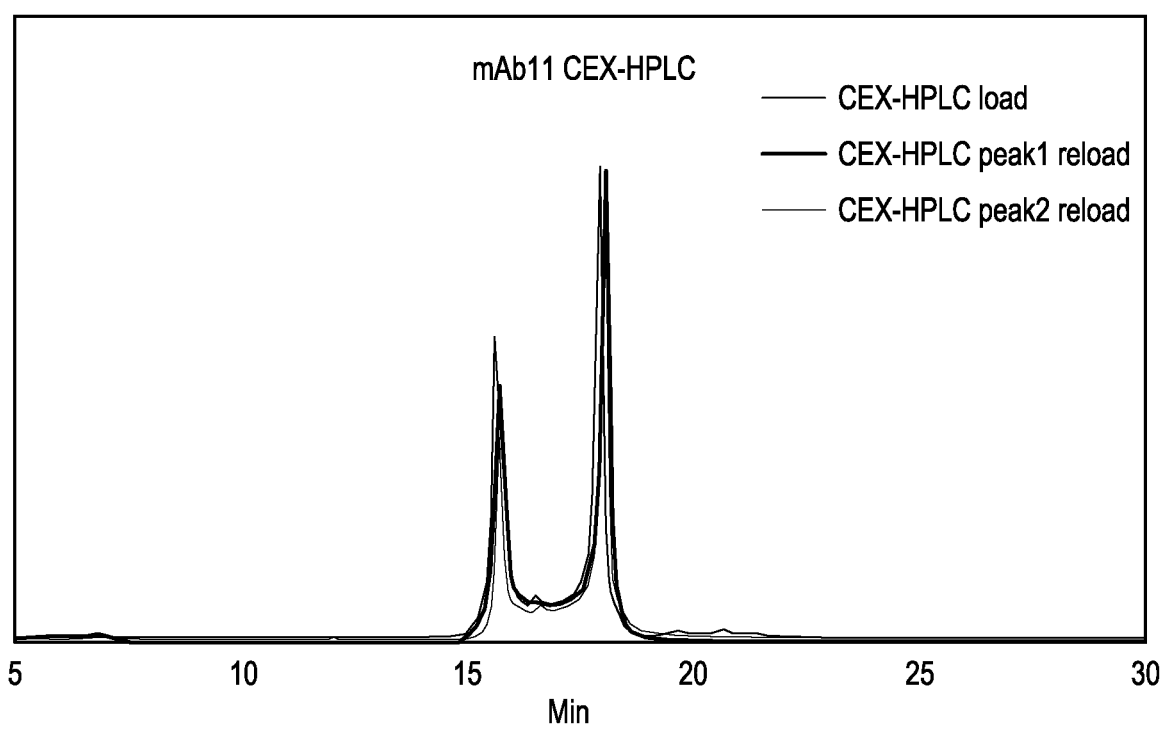
FIG. 4 shows CEX-HPLC chromatogram for mAb11 and reinjection of peak 1 and peak 2. Reinjection of peak 1 and peak 2 still resulted in two similar elution patterns. The CEX-HPLC method used salt gradient elution with 20 mM MES to 20 mM MES, 1 M NaCl at different pH (0-60 min) with a constant total injected protein mass of 10 μg.
Figure 5:
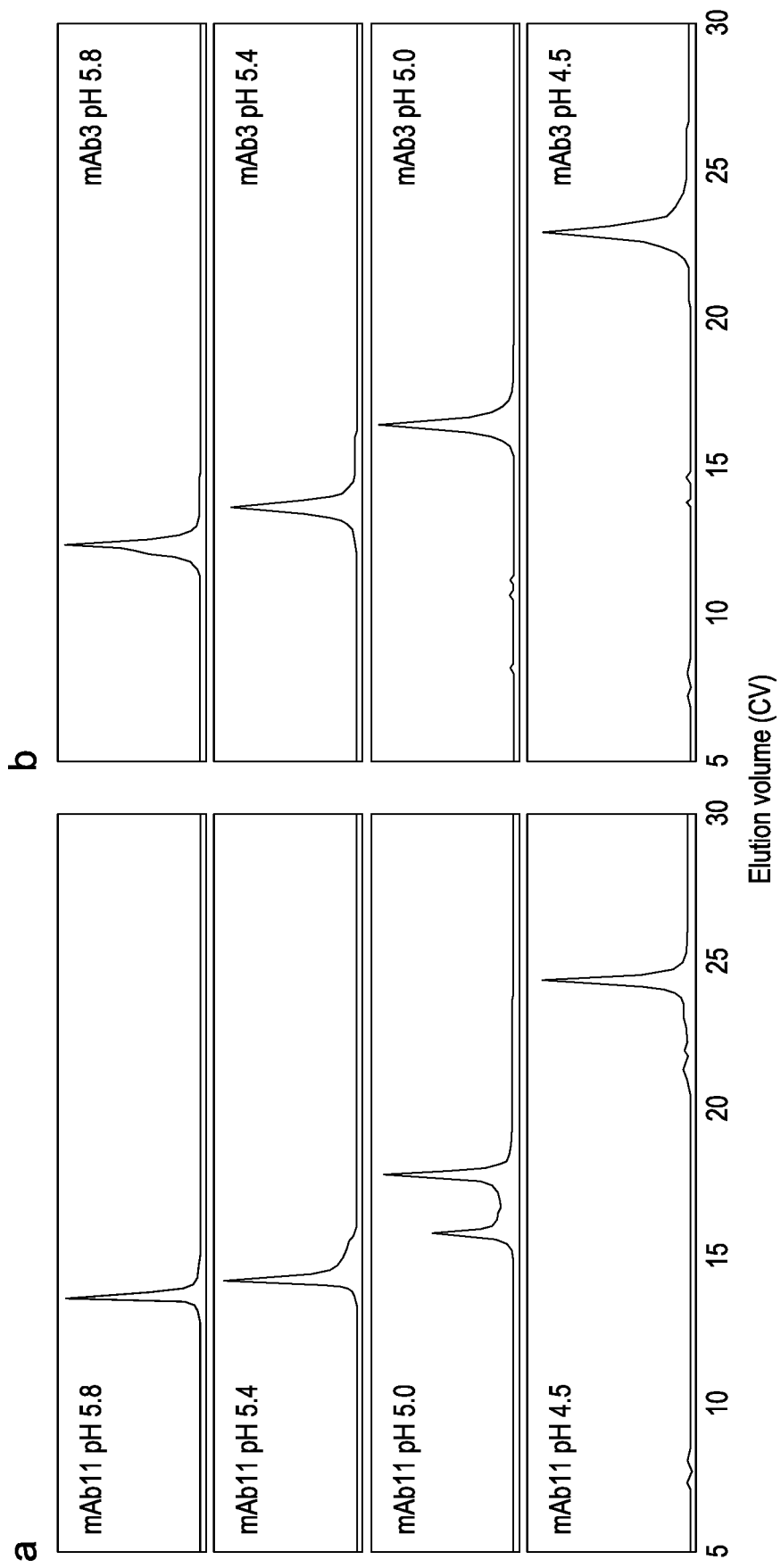
FIG. 5a shows CEX-HPLC chromatogram for mAb11 at different pHs. The two-peak elution behavior was observed at pH 5.0. Changing the pH changed the ratio of the two peaks. Increasing the pH resulted in higher percentage of the first peak, while lowering pH resulted in higher percentage of the second peak.
FIG. 5b shows CEX-HPLC chromatogram for mAb3 at different pHs. The single-peak elution behavior was observed at different pHs for ipilimumab. The CEX-HPLC method used salt gradient elution with 20 mM MES to 20 mM MES, 1 M NaCl at varying pH (0-60 min) with a constant total injected protein mass of 10 μg.
Figure 6:
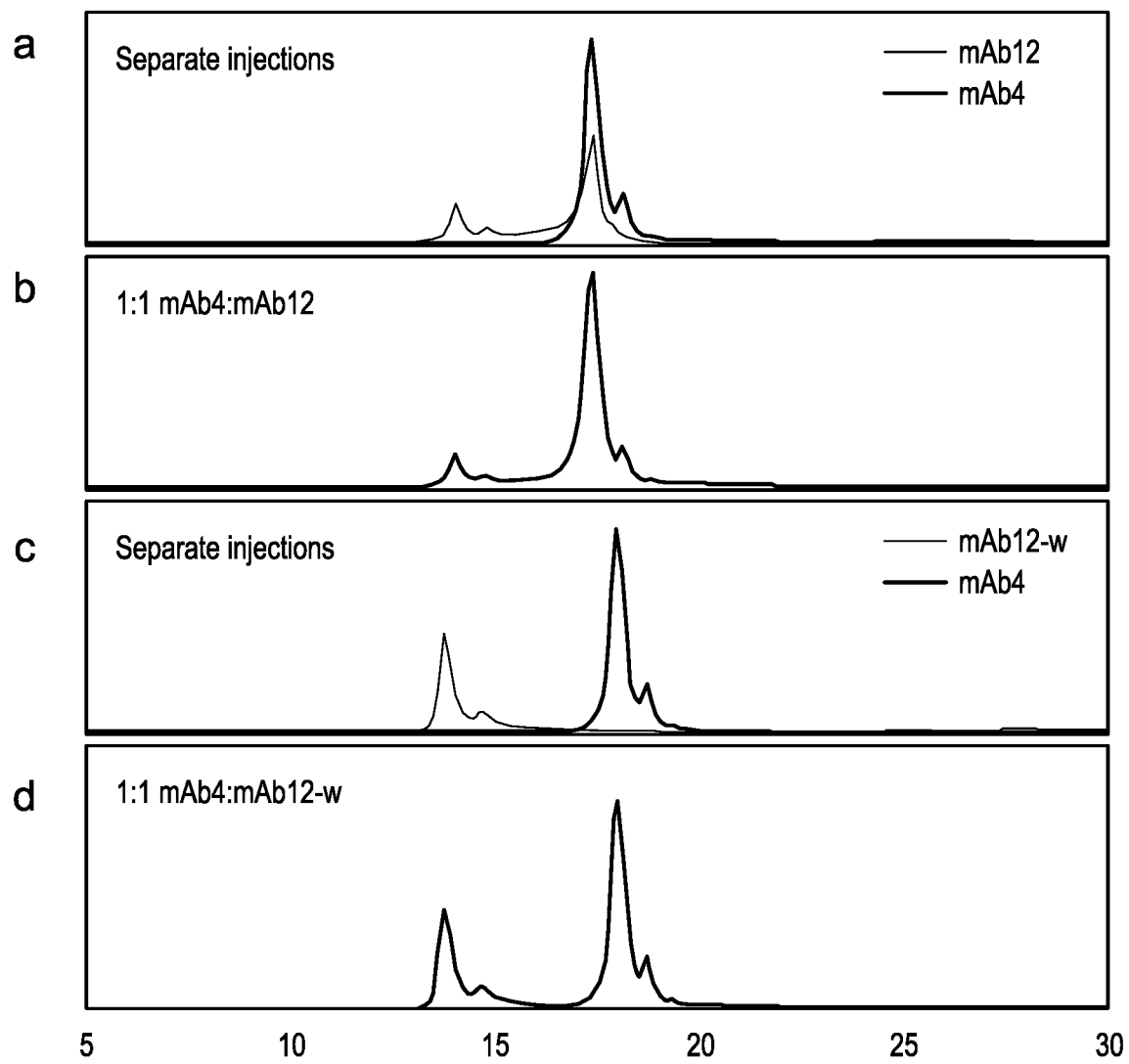
FIGS. 6a-6b show exemplary CEX-HPLC e-grams of mAb4 and mAb12 with separate injections (a) or the combo antibodies at 1:1 ratio (b). As mAb12 has broad two-peak elution behavior, it overlays with mAb4, making it difficult for the charge variant characterization when injecting the two combo antibodies at ratio 1:1 onto the CEX column.
FIGS. 6c-6d show exemplary CEX-HPLC e-grams of mAb4 and mAb12 with separate injections (c) or the combo antibodies at 1:1 ratio (d). As mAb12-w has narrow single-peak elution behavior, it did not overlay with mAb4, making it easy for the charge variant characterization when injecting the two combo antibodies at ratio 1:1 onto the CEX column. The charge variant profile of both antibodies was thus retained and could be clearly characterized. The CEX-HPLC method used salt gradient elution with 20 mM MES, pH 5.0 to 20 mM MES, 600 mM NaCl, pH 5.0 (0-60 min) with a constant total injected protein mass of 10 μg.
Figure 7:
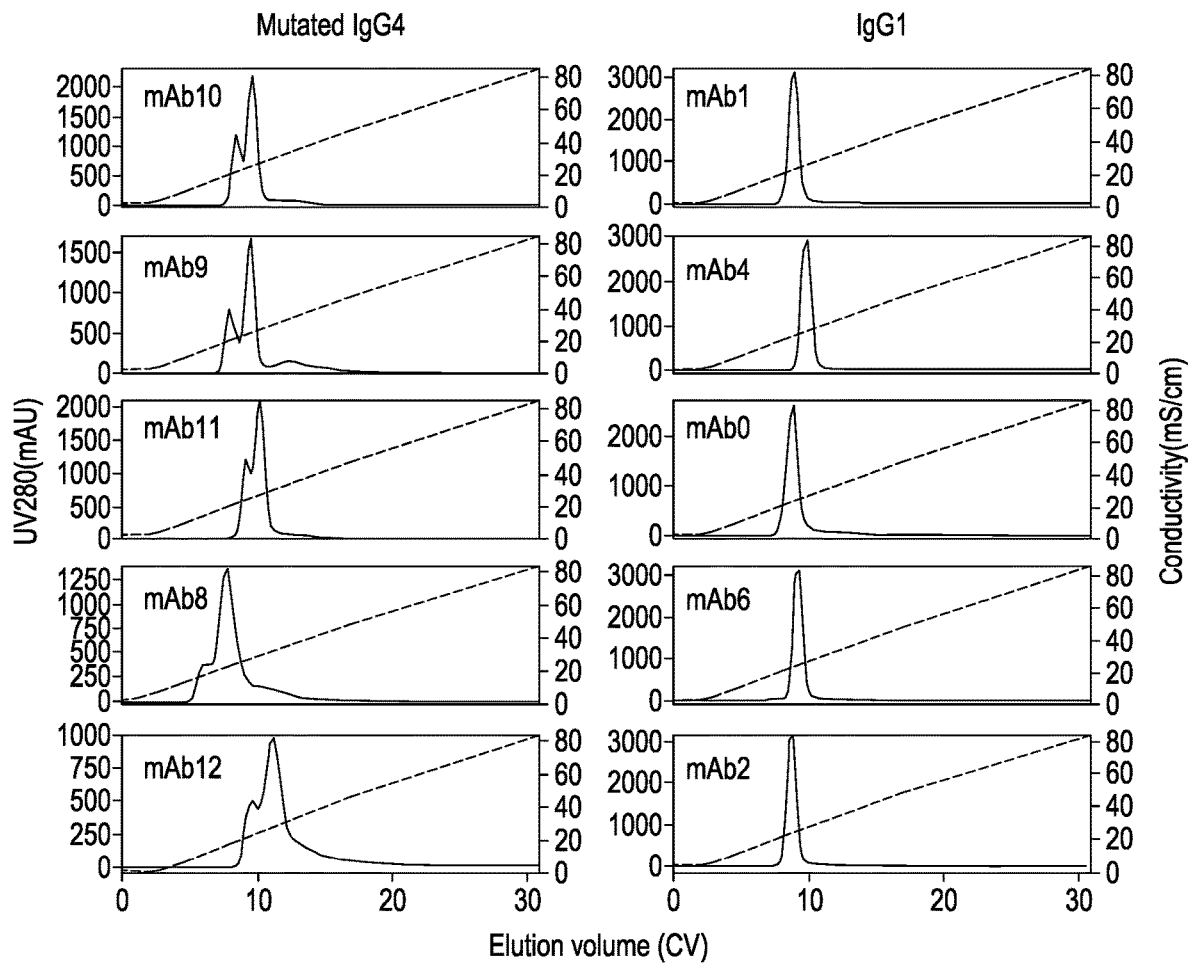
FIG. 7 shows that two-peak elution behaviors was also observed on preparative CEX resin for IgG4 but not IgG1. 40 mM sodium acetate with sodium chloride (0-1.0 M) in 30 CV, pH=5.0; Resin: Poros XS with 10 g/L resin loading.
Figure 8:
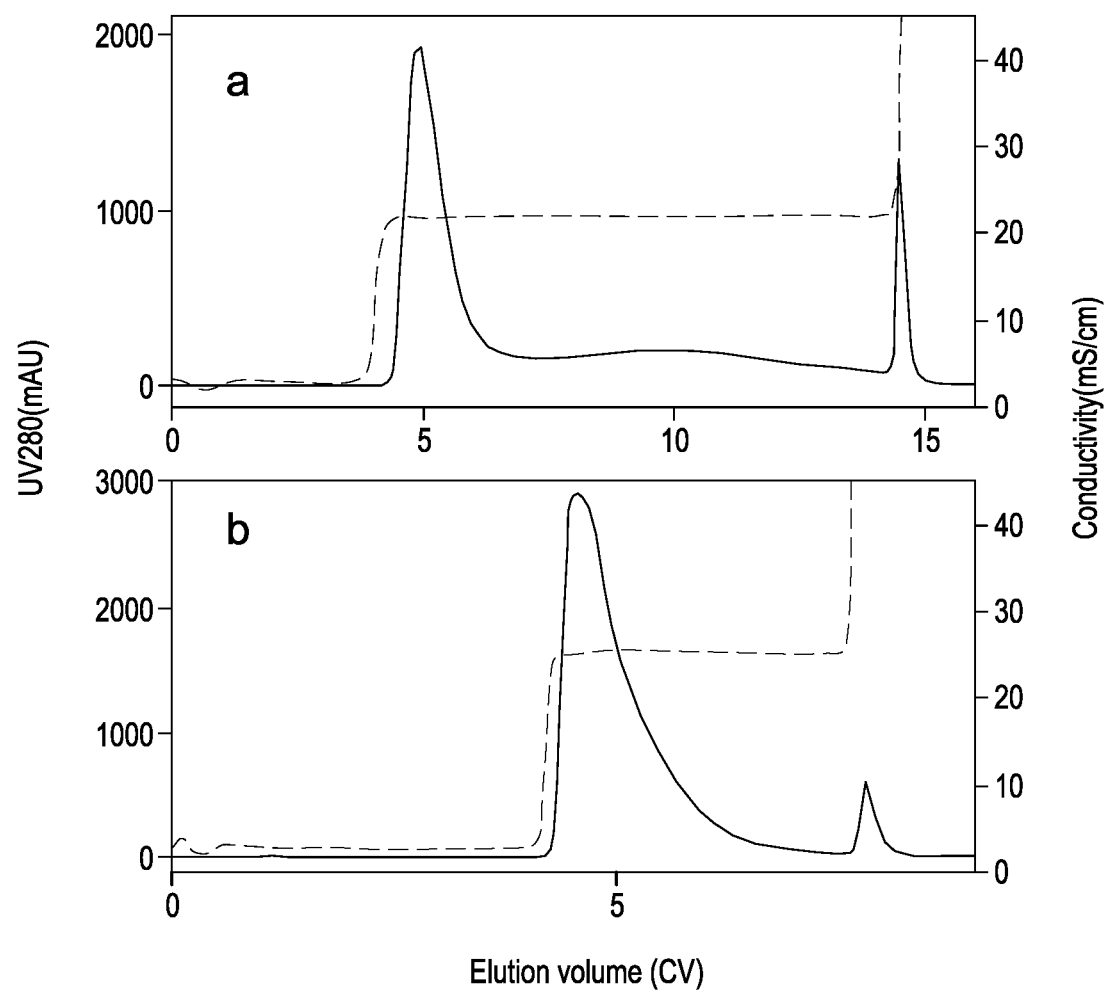
FIGS. 8a-8b show salt step elution at different conductivity for mAb10. (a) The salt step elution chromatogram at lower conductivity; (b) The salt step elution chromatogram at higher conductivity. The two conductivities can be found during the salt gradient elution at pH 5.0 in FIG. 7.

The two peaks were isolated, and the peak fractions were injected on the size exclusion chromatography (SEC) column. The two SEC chromatograms (FIG. 2) overplayed very well with more than 99% purity, indicating no size difference or aggregate formation for the two peaks. Similar charge profiles were observed for peak1 and peak2 (FIG. 3), suggesting that no major charge difference for these two peaks. The two-peak fractions were also individually re-injected on the CEX column under the same conditions. Re-injecting of the two fractions gave exactly the same two-peak elution behavior as the original mutated IgG4 (FIG. 4), suggesting that there may be two different binding conformations for the mutated IgG4 on the resin and the two populations were interchangeable after elution. The two-peak ratio changed when changing the CEX operating pH. Increasing pH resulted in higher percentage of first peak, while lowering pH results in higher percentage of second peak (FIG. 5). The two-peak elution behavior of the mutated IgG4 poses challenges on analytical CEX-HPLC method development for charge variance analysis as an example. The two-peak elution makes it difficult to quantify the charge variant profile as the two peak were not separated based on charge difference, and the ratio of the two-peak can be changed by changing the operating conditions (e.g., pH). Furthermore, combination therapy has recently become the most promising immune-stimulatory cancer theory, and development of robust analytical method for combination charge variant analysis is urgently needed. The double peak elution behavior of IgG4 (SERINE-TO-PROLINE (CPPC)) leads to broad elution profile on CEX-HPLC, which will usually causes chromatogram interferences with the combining molecules, making it impossible for combo drug charge variant characterization (FIG. 6). The two-peak elution behaviors were also observed on preparative CEX resin (FIG. 7), making it difficult to develop robust commercial CEX purification process. mAb10 was used as an example here. As two peak elution behavior was observed during the salt gradient elution, different conductivity conditions can be used during the step elution. As shown in FIG. 8, lower elution conductivity gave broad elution CV (FIG. 8a), while higher conductivity gave small elution CV (FIG. 8b). However, higher conductivity resulted in higher impurity level and HMW level in the elution pool as shown in Table 3. The elution condition was chosen based on the salt gradient elution at pH5. Two different elution conditions corresponding to the two peak conductivity during salt gradient elution were used.

TABLE 3

Impact of two-peak elution behavior on commercial CEX purification process development.

| Molecule | Elution condition | HCP/ ppm | SEC-HPLC | | | Pool volume (CV) |
| | | | HMW (%) | LMW (%) | Mono (%) | |
| --- | --- | --- | --- | --- | --- | --- |
| mAb10 | First peak conductivity | 18 | 0.9 | 0 | 99.1 | 8.9 |
| | Second peak conductivity | 24 | 0.9 | 0.1 | 99.0 | 2.4 |
| mAb9 | First peak conductivity | 10 | 0.6 | 0 | 99.4 | 10.0 |
| | Second peak conductivity | 15 | 1.9 | 2.2 | 95.9 | 2.0 |
| mAb8 | First peak conductivity | 9 | 0.7 | 0.1 | 99.2 | 10.0 |
| | Second peak conductivity | 15 | 0.9 | 0.8 | 98.3 | 2.8 |

Figure 9:
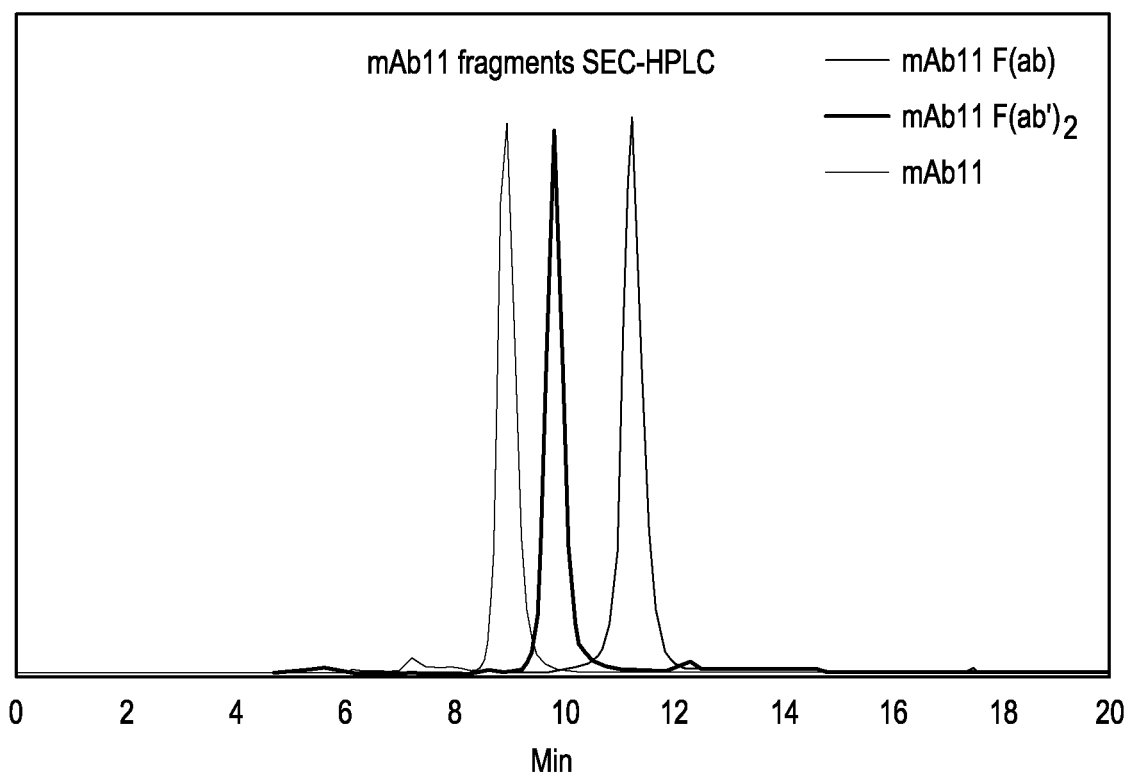
FIG. 9 shows SEC-HPLC chromatogram for mAb11 and its fragments. SEC profile indicated the successful generation of high purity F(ab')$_2$ and F(ab) fragments using pepsin and papain respectively.
Figure 10:
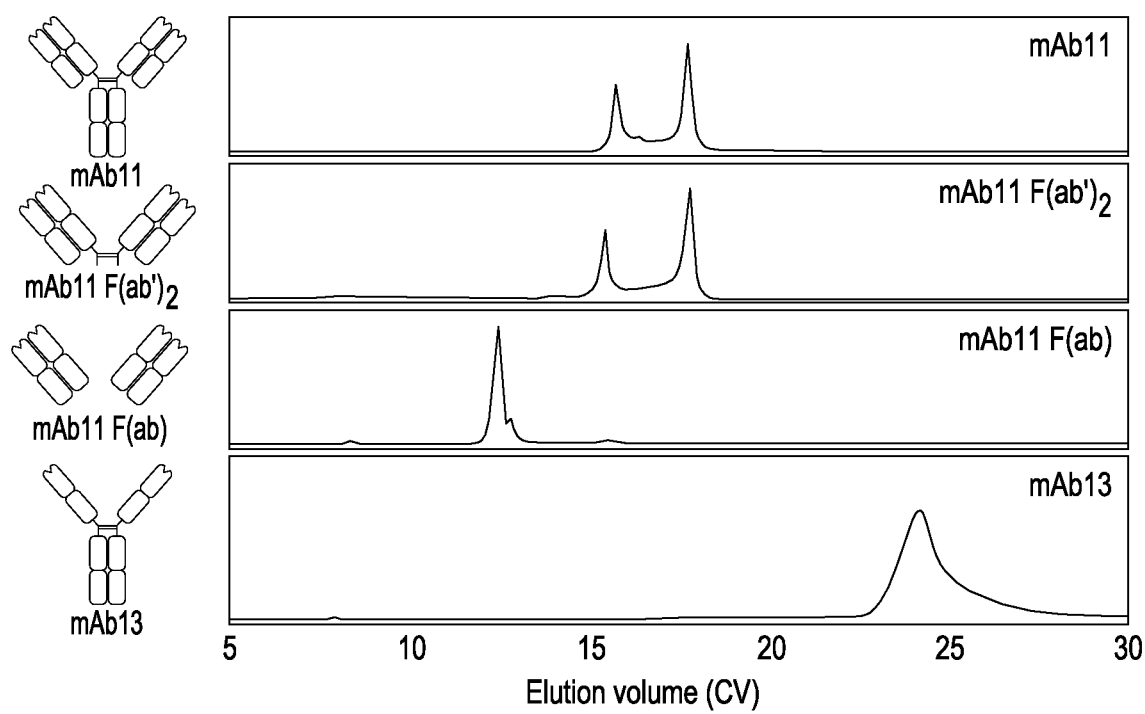
FIG. 10 shows CEX-HPLC chromatogram for mAb11 and its fragments. mAb11 F(ab')$_2$ fragment was generated using Immobilized Pepsin (Thermo Fisher Scientific). mAb11F(ab) fragment was generated using Immobilized papain (Thermo Fisher Scientific). Two-peak elution behavior was observed for mAb11 as expected. Two-peak elution behavior was also observed for mAb11 F(ab')$_2$ fragment, suggesting that that F(ab')$_2$, not Fc, may be contributing to the two-peak elution behavior. mAb13, an Fc fusion protein with IgG4 (SERINE-TO-PROLINE (CPPC)) Fc tail, was also tested on the CEX-HPLC column. The single-peak elution behavior for mAb13 on CEX column further confirms that Fc tail is not involved in the two-peak elution behavior. In an attempt to further narrow down the IgG4 fragment that might be responsible for the two-peak elution behavior, F(ab) was also injected on the CEX-HPLC column. Interestingly, single-peak elution behavior, instead of two-peak elution behavior, was observed for F(ab). This results suggest the important role of IgG4 (SERINE-TO-PROLINE (CPPC)) hinge plays in the two-peak elution behavior. It is thus concluded that the presence of IgG4 (SERINE-TO-PROLINE (CPPC)) F(ab')2 is responsible for the two-peak elution behavior.

In order to better understand the two-peak elution behaviors for IgG4 (SERINE-TO-PROLINE (CPPC)) from structure perspective, enzymatic generation of mAb fragments were performed. Immobilized Pepsin and immobilized Papain was used to generate F(ab')2 and F(ab) Fragment of mAb11 (detailed in the method section). F(ab')2 differs from F(ab) in that it is the connection of two F(ab) with IgG4 hinge. SEC-HPLC profile (FIG. 9) suggests the successful generation of high purity F(ab')2 and F(ab) using pepsin and papain respectively. mAb 11 F(ab')2 was first injected on the CEX-HPLC column under the same conditions as full mAb11. As shown in FIG. 10, two peak elution behavior was also observed for mAb11 F(ab')$_2$ fragment, suggesting that F(ab')$_2$, not Fc tail, may be responsible for the two-peak elution behavior. mAb13, an Fc fusion protein with IgG4 (SERINE-TO-PROLINE (CPPC)) Fc tail, was also tested on the CEX-HPLC column. The single-peak elution behavior for mAb13 (FIG. 10) on CEX column further confirms that Fc tail is not involved in the two-peak elution behavior. In an attempt to further narrow down the IgG4 fragment that might be responsible for the two-peak elution behavior, F(ab) was also injected on the CEX-HPLC column. Interestingly, single-peak elution behavior, instead of two-peak elution behavior, was observed for F(ab). This results suggest the important role of IgG4 (SERINE-TO-PROLINE (CPPC)) hinge plays in the two-peak elution behavior. It is thus concluded that the presence of IgG4 (SERINE-TO-PROLINE (CPPC)) F(ab')2 is responsible for the two-peak elution behavior.

Single-point mutagenesis on current IgG4 (SERINE-TO-PROLINE (CPPC)) sequence was explored for the potential of designing next generation therapeutic IgG4 for improved bioanalytical and bioprocessing properties. Initially, SERINE-TO-PROLINE (CPPC) mutation of wild-type IgG4 was designed to mimic IgG1 hinge with CPPC motif to prevent Fab arm-exchange, but this mutation also created undesirable two-peak elution behavior on CEX column in certain solution condition. It is desirable that another single-point mutation for current IgG4 (SERINE-TO-PROLINE (CPPC)) would prevent Fab-arm exchange and improve bioanalytical and bioprocessing properties as well. A similar approach to the hinge SERINE-TO-PROLINE (CPPC) mutation was tried to achieve such properties by mutating a single amino acid of IgG4 (SERINE-TO-PROLINE (CPPC)) to corresponding amino acid in IgG1. As IgG4 (SERINE-TO-PROLINE (CPPC)) F(ab')2 has been identified to be responsible for the two-peak elution behavior, Fc region was not considered during the sequence alignment. All the IgG1 and IgG4 in FIG. 1 has the same kappa light chain, thus light chain sequence was not aligned. As each antibody has its own unique Variable heavy ($V_H$) region, $V_H$ region of IgG4 cannot be responsible for the two-peak elution behavior and it is also excluded from the sequence alignment. Thus, amino acid sequence alignment for IgG4 (SERINE-TO-PROLINE (CPPC)) and IgG1 was performed for constant heavy chain 1(CH1) and hinge region as shown in FIG. 11. Total 12 amino acid differences are identified between IgG4 (SERINE-TO-PROLINE (CPPC)) and IgG1, and are highlighted with green and yellow. The first identified cysteine amino acid in IgG4 forms the inter-chain disulfide bond between heavy and light chain, thus cysteine was not mutated to corresponding serine to preserve IgG4 intact structure. The rest 11 amino acids in IgG4 (SERINE-TO-PROLINE (CPPC)) were mutated to corresponding amino acid individually in IgG1 to evaluate their impact on CEX-HPLC column behavior.

Figure 12:
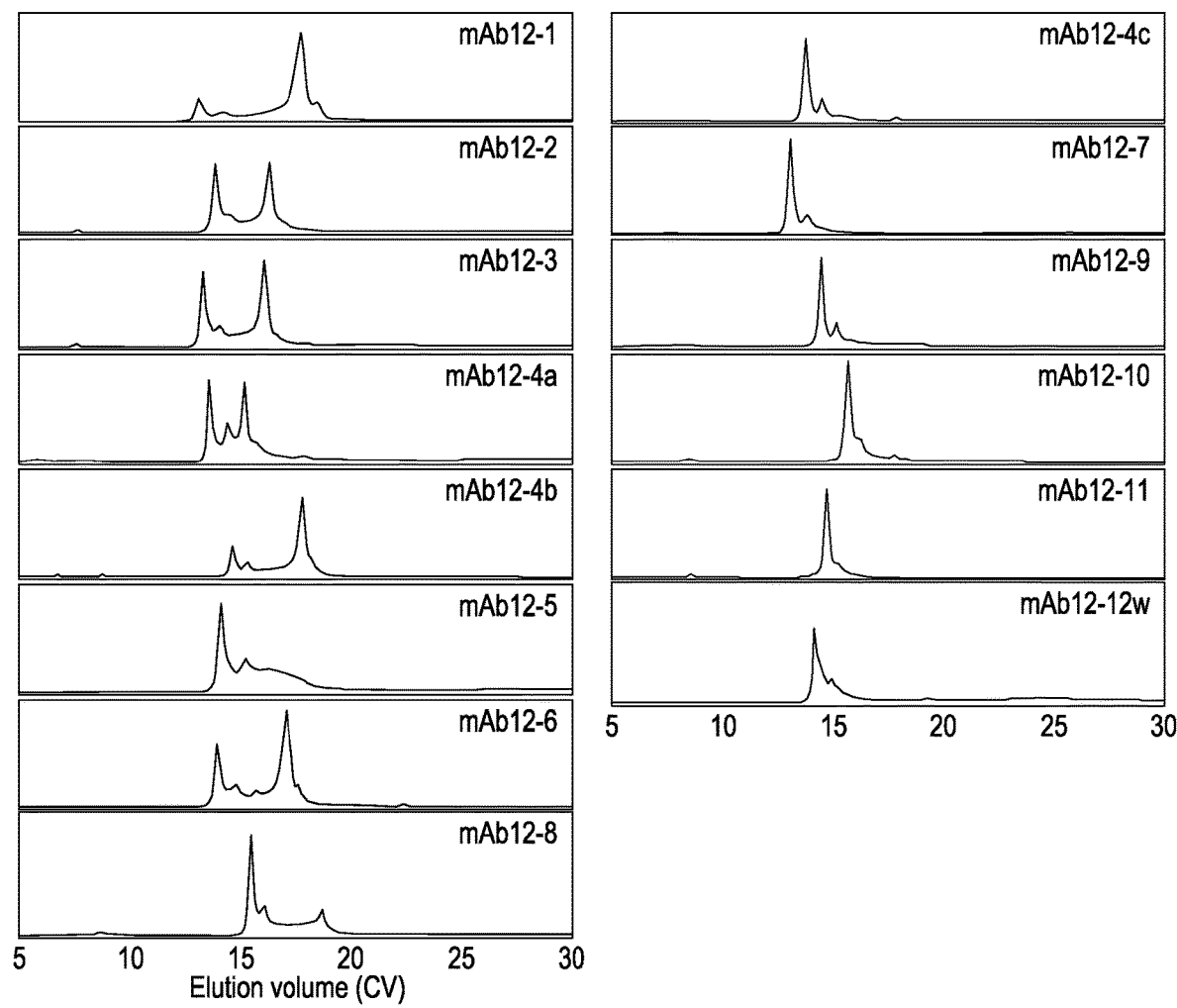
FIG. 12 shows CEX-HPLC chromatogram for the mutants. Single-peak elution behaviors was observed for mAb12-4c, mAb12-7, mAb12-9, mAb12-10, mAb12-11 and mAb12-w. mAb12-w is the wild-type mAb12 without the mutation of serine-to-proline in the hinge region. The CEX-HPLC method used salt gradient elution with 20 mM MES, pH 5.0 to 20 mM MES, 600 mM NaCl, pH 5.0 (0-60 min) with a constant total injected protein mass of 10 μg.
Figure 13:
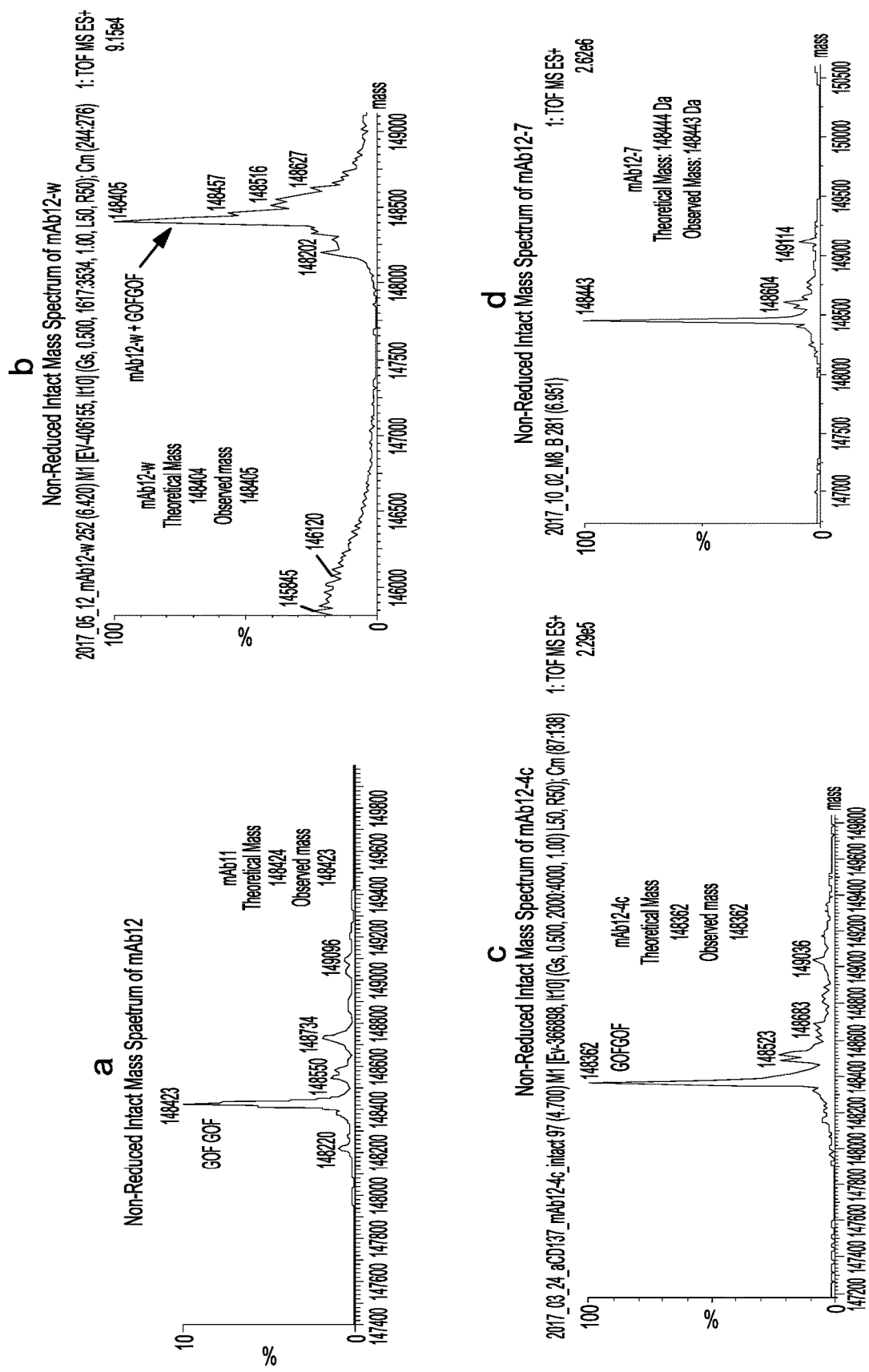
FIGS. 13a-13h show non-reduced intact mass of the mutants. Non-reduced intact mass spectrum confirms the successful expression of mAb12, mAb12-w, mAb12-4c, mAb12-7, mAb12-9, mAb12-10, mAb12-11 and HCA195 (wild-type Recombinant Human IgG4 kappa from bio-rad).
Figure 14:
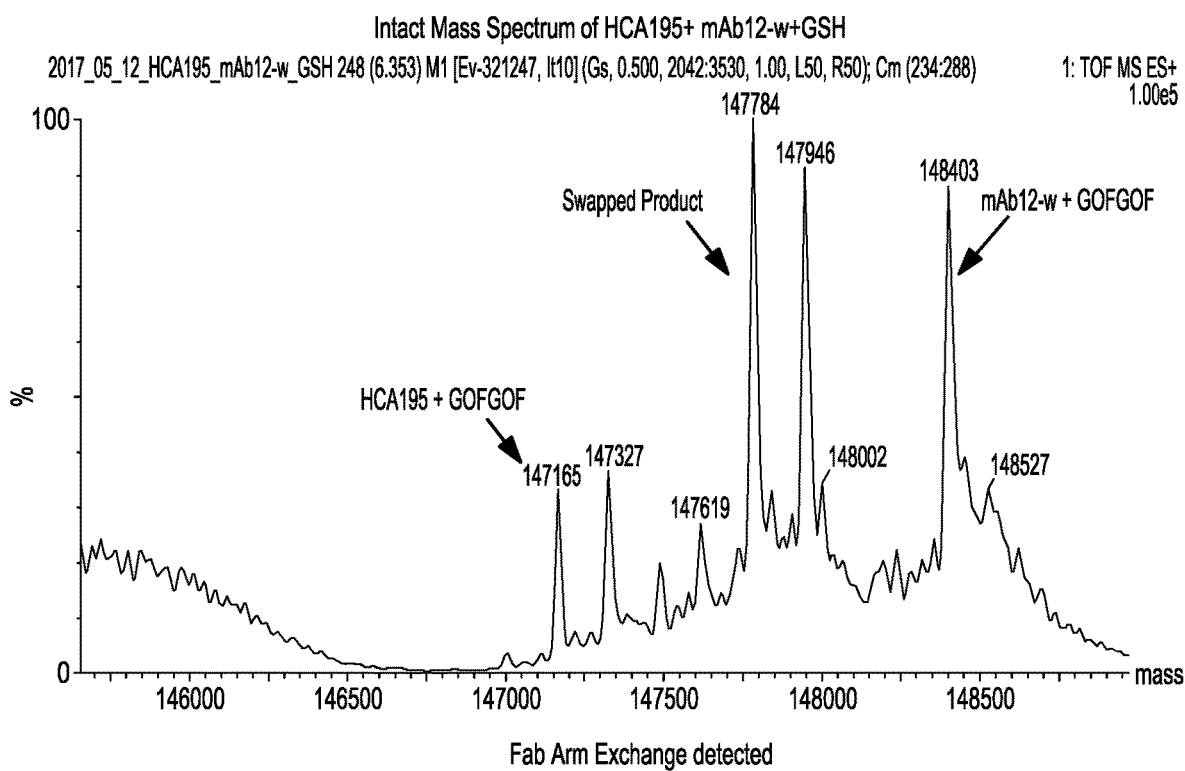
FIG. 14 shows non-reduced intact mass of Fab-arm exchange phenomena of HCA195 and mAb12-w. Both mAb12-w and HCA195 are wild type IgG4 without CPPC mutation in the hinge region. Fab-arm exchange was detected as a new bispecific antibody peak was observed. mAb12-w was mixed with HCA195 and incubated with 0.5 mM reduced glutathione (GSH; Sigma) in degassed PBS (pH7.2). The final concentration of both mAb12-w and HCA195 was 20 μg/mM. The mixtures (70 μL) were incubated at 37 degree for 24 h. The samples were then stored at 4 degree before intact mass testing.
Figure 15:
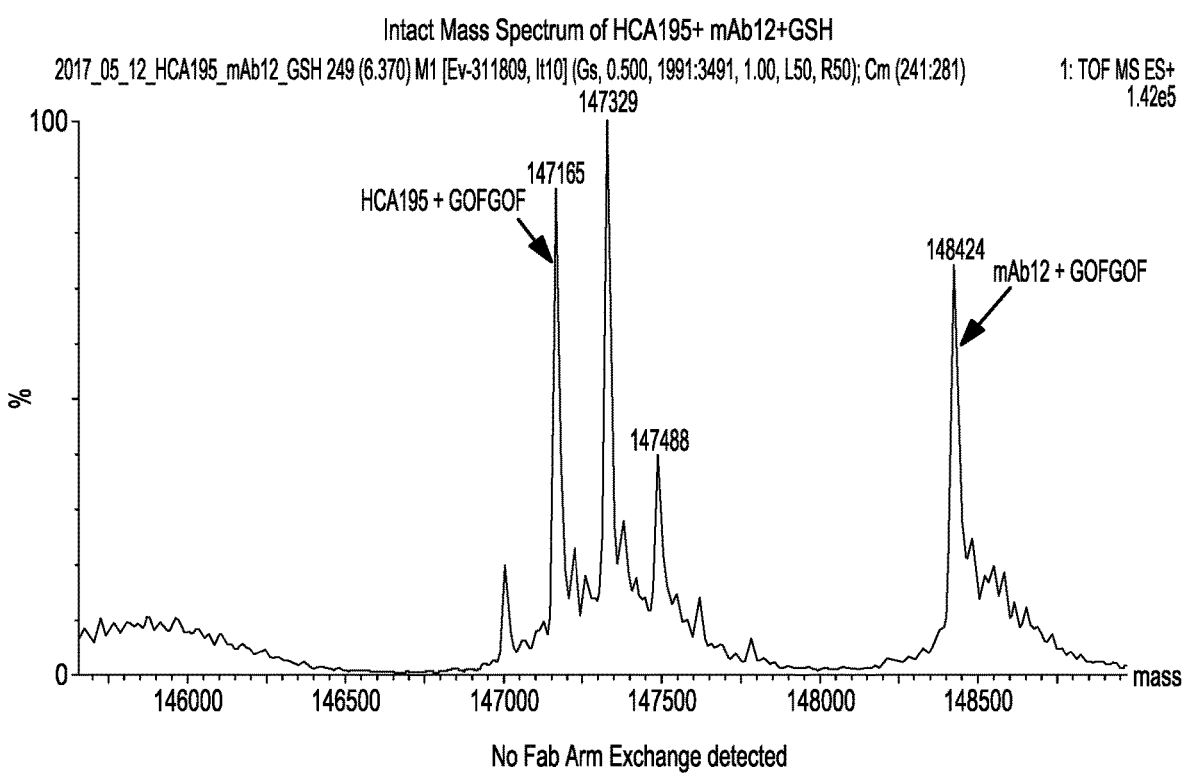
FIG. 15 shows non-reduced intact mass of Fab-arm exchange results of HCA195 and mAb12. No fab-arm exchange was detected as mAb12 contains the CPPC motif in the hinge region.
Figure 16:
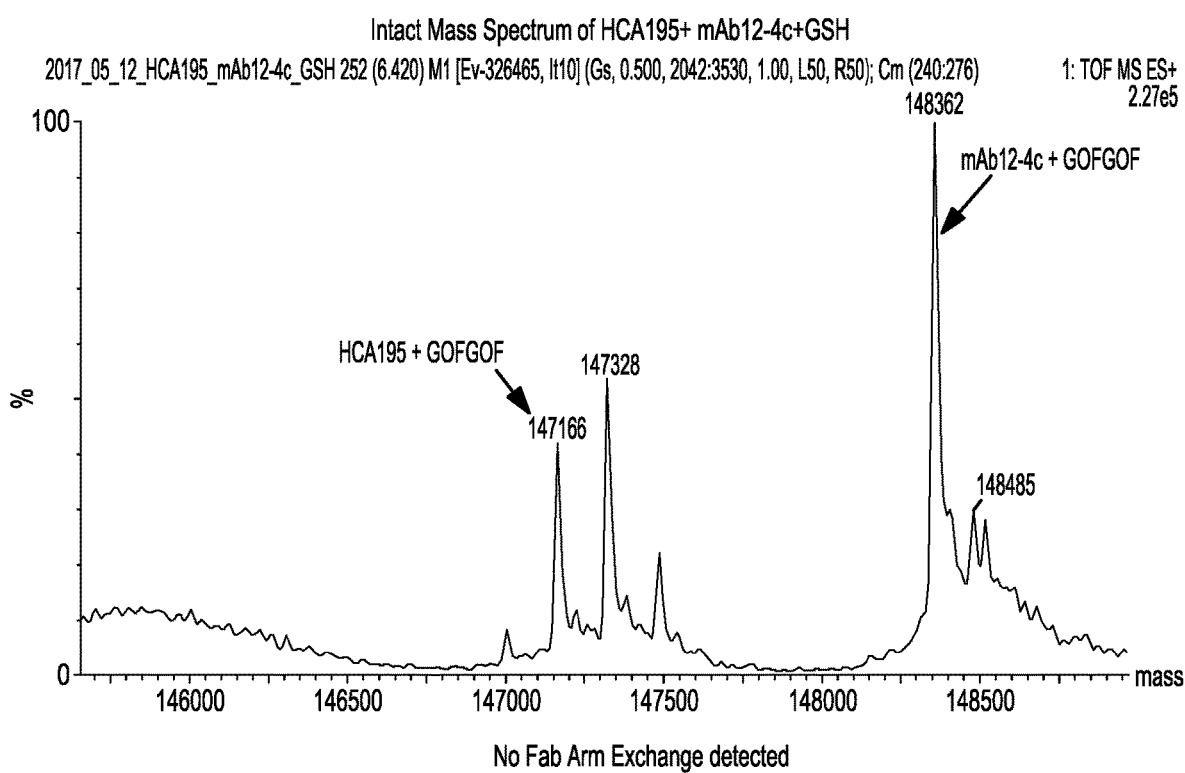
FIG. 16 shows non-reduced intact mass of Fab-arm exchange results of HCA195 and mAb12-4c. No fab-arm exchange was detected as mAb12-4c contains the CPPC motif in the hinge region.
Figure 17:
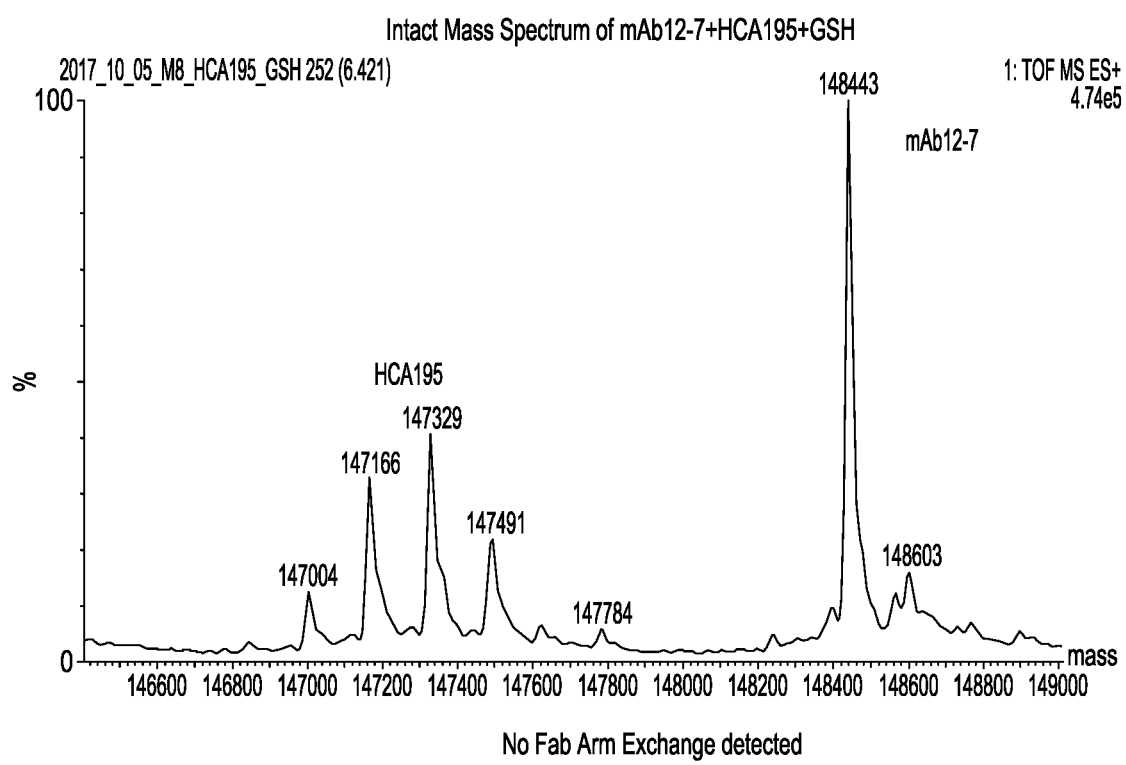
FIG. 17 shows non-reduced intact mass of Fab-arm exchange results of HCA195 and mAb12-7. No fab-arm exchange was detected as mAb12-7 contains the CPPC motif in the hinge region.
Figure 18:
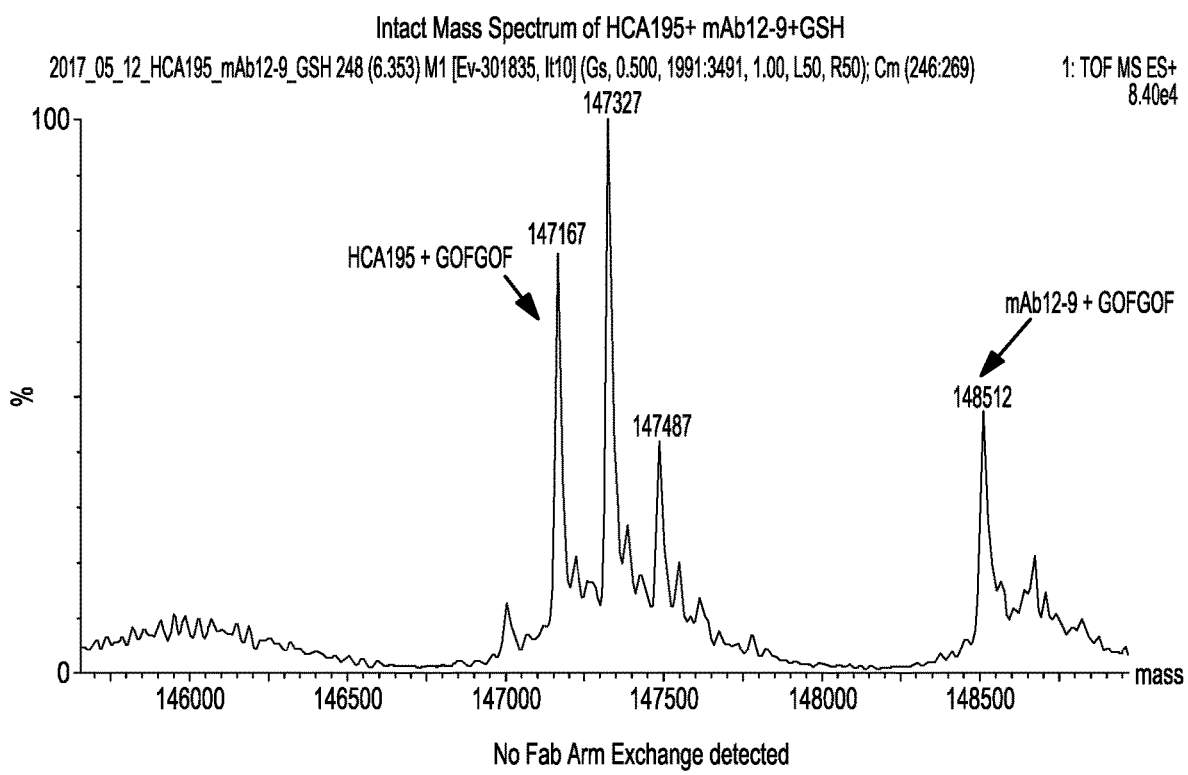
FIG. 18 shows non-reduced intact mass of Fab-arm exchange results of HCA195 and mAb12-9. No fab-arm exchange was detected as mAb12-9 contains the CPPC motif in the hinge region.
Figure 19:
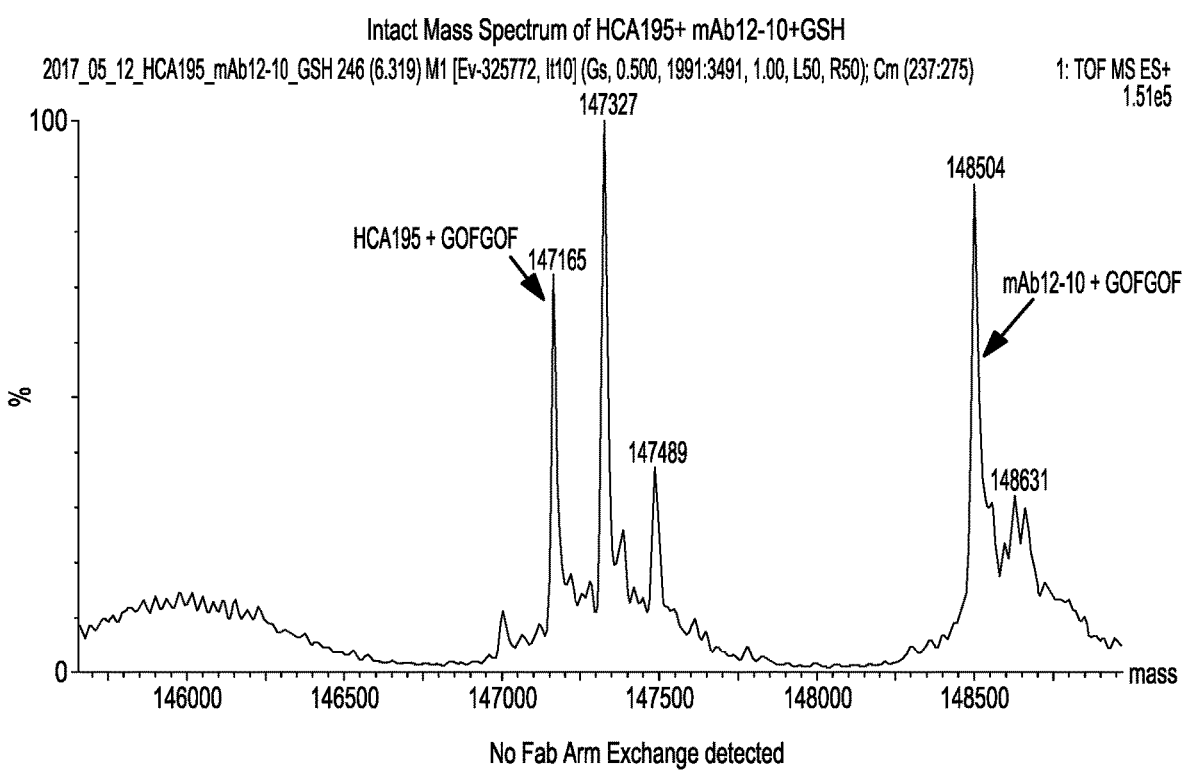
FIG. 19 shows non-reduced intact mass of Fab-arm exchange results of HCA195 and mAb12-10. No fab-arm exchange was detected as mAb12-10 contains the CPPC motif in the hinge region.
Figure 20:
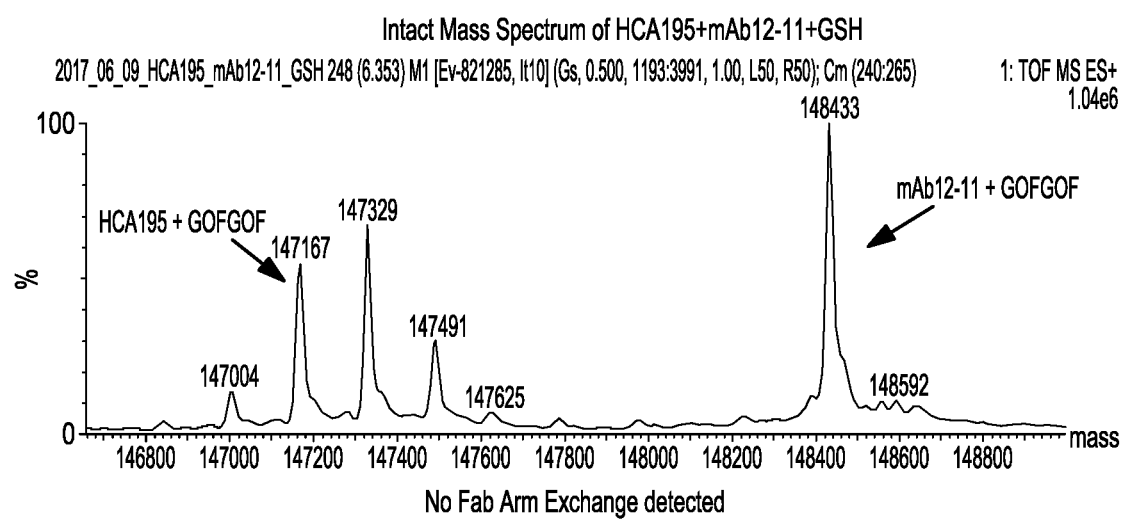
FIG. 20 shows non-reduced intact mass of Fab-arm exchange results of HCA195 and mAb12-11. No fab-arm exchange was detected as mAb12-11 contains the CPPC motif in the hinge region.
Figure 21:
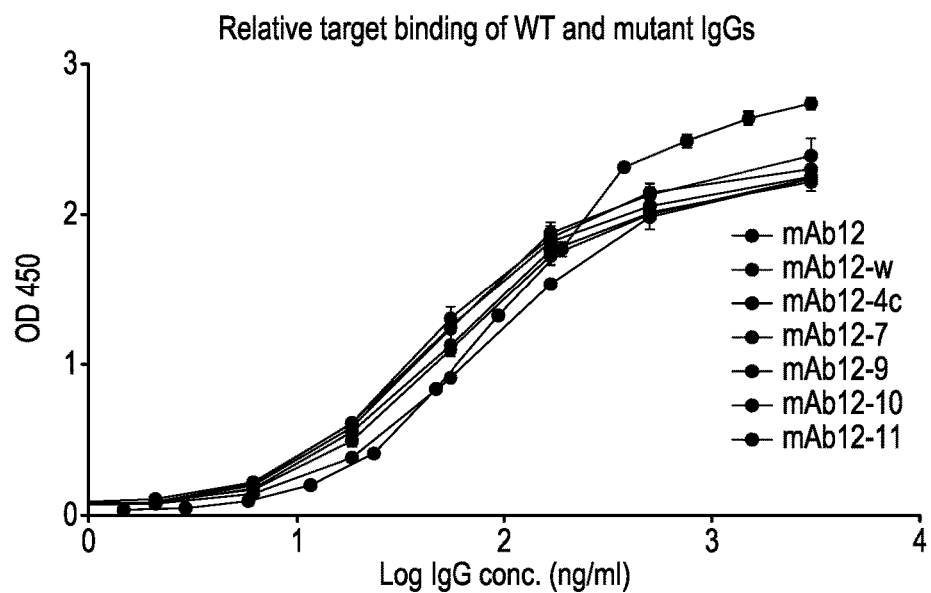
FIG. 21 shows ELISA binding assay for the mAb12 mutations. ELISA binding assay suggest that all the mutants has reasonable binding as the mAb12. The mutation did not alter the binding activity of mAb12.

CEX-HPLC chromatograms for therapeutic mAb12 mutants were shown in FIG. 12. Single-peak elution behaviors were observed for mAb12-4c, mAb12-7, mAb12-9, mAb12-10, mAb12-11, and mAb12-w. Intact mass confirmed the successful mutation of these mutants (FIG. 13). mAb12-w is the wild-type mAb12 without the mutation of serine-to-proline in the hinge region; mAb12-w can exchange Fab-arm with another wild-type IgG (HCA195) to form bispecific, as confirmed by intact mass (FIG. 14). Serine 228 was muted to proline (mAb12) to prevent fab-arm exchange (FIG. 15). This mutation, however, created unexpected two-peak elution behavior on the CEX-HPLC. The unexpected double peak elution behavior for mAb12 can be eliminated by the additional single-point mutation of Lysine 196 to proline (mAb12-4c), or serine 217 to proline (mAb12-7), or glycine 220 to threonine (mAb12-9), or proline 224 to histidine (mAb12-10), or proline 225 to threonine (mAb12-11). Intact mass also confirms that these mutants cannot exchange Fab-arm with wild-type IgG as shown in (FIGS. 16-20). ELISA binding assay (FIG. 21) suggested that all the mutants had reasonable binding activity as the mAb12. The mutation did not alter the binding activity of mAb12.

REFERENCE

[1] Y. M. Lucisano Valim, P. J. Lachmann, The effect of antibody isotype and antigenic epitope density on the complement-fixing activity of immune complexes: a systematic study using chimaeric anti-NIP antibodies with human Fc regions, Clinical and experimental immunology, 84 (1991) 1-8.
[2] J. S. van der Zee, P. van Swieten, R. C. Aalberse, Serologic aspects of IgG4 antibodies. II. IgG4 antibodies form small, nonprecipitating immune complexes due to functional monovalency, The Journal of Immunology, 137 (1986) 3566-3571.
[3] J. Schuurman, R. Van Ree, G. J. Perdok, H. R. Van Doom, K. Y. Tan, R. C. Aalberse, Normal human immunoglobulin G4 is bispecific: it has two different antigen-combining sites, Immunology, 97 (1999) 693-698.
[4] M. van der Neut Kolfschoten, J. Schuurman, M. Losen, W. K. Bleeker, P. Martinez-Martinez, E. Vermeulen, T. H. den Bleker, L. Wiegman, T. Vink, L. A. Aarden, M. H. De Baets, J. G. van de Winkel, R. C. Aalberse, P. W. Parren, Anti-inflammatory activity of human IgG4 antibodies by dynamic Fab arm exchange, Science (New York, N.Y.), 317 (2007) 1554-1557.
[5] J. P. Silva, O. Vetterlein, J. Jose, S. Peters, H. Kirby, The S229P mutation prevents in vivo and in vitro IgG4 Fab-arm exchange as demonstrated using a combination of novel quantitative immunoassays and physiological matrix preparation, J Biol Chem, 290 (2015) 5462-5469.
[6] T. Rispens, P. Ooijevaar-de Heer, O. Bende, R. C. Aalberse, Mechanism of immunoglobulin G4 Fab-arm exchange, J Am Chem Soc, 133 (2011) 10302-10311.
[7] A. M. Davies, T. Rispens, T. H. den Bleker, J. M. McDonnell, H. J. Gould, R. C. Aalberse, B. J. Sutton, Crystal structure of the human IgG4 C(H)3 dimer reveals the role of Arg409 in the mechanism of Fab-arm exchange, Mol Immunol, 54 (2013) 1-7.
[8] A. M. Davies, T. Rispens, T. H. den Bleker, J. M. McDonnell, H. J. Gould, R. C. Aalberse, B. J. Sutton, Crystal structure of the human IgG4 CH3 dimer reveals the role of Arg409 in the mechanism of Fab-arm exchange, Molecular Immunology, 54 (2013) 1-7.
[9] J. W. Bloom, M. S. Madanat, D. Marriott, T. Wong, S. Y. Chan, Intrachain disulfide bond in the core hinge region of human IgG4, Protein science: a publication of the Protein Society, 6 (1997) 407-415.
[10] S. Angal, D. J. King, M. W. Bodmer, A. Turner, A. D. G. Lawson, G. Roberts, B. Pedley, J. R. Adair, A single amino acid substitution abolishes the heterogeneity of chimeric mouse/human (IgG4) antibody, Molecular Immunology, 30 (1993) 105-108.
[11] C. Wang, K. B. Thudium, M. Han, X. T. Wang, H. Huang, D. Feingersh, C. Garcia, Y. Wu, M. Kuhne, M. Srinivasan, S. Singh, S. Wong, N. Garner, H. Leblanc, R. T. Bunch, D. Blanset, M. J. Selby, A.J. Korman, In vitro characterization of the anti-PD-1 antibody nivolumab, BMS-936558, and in vivo toxicology in non-human primates, Cancer immunology research, 2 (2014) 846-856.
[12] A. M. Davies, B. J. Sutton, Human IgG4: a structural perspective, Immunological Reviews, 268 (2015) 139-159.
[13] G. Scapin, X. Yang, W. W. Prosise, M. McCoy, P. Reichert, J. M. Johnston, R. S. Kashi, C. Strickland, Structure of full-length human anti-PD1 therapeutic IgG4 antibody pembrolizumab, Nature structural & molecular biology, 22 (2015) 953-958.
[14] J. M. Reichert, Antibodies to watch in 2017, mAbs, 9 (2017) 167-181.
[15] J. G. Salfeld, Isotype selection in antibody engineering, Nat Biotech, 25 (2007) 1369-1372.
[16] A. F. Labrijn, A. O. Buijsse, E. T. van den Bremer, A. Y. Verwilligen, W. K. Bleeker, S. J. Thorpe, J. Killestein, C. H. Polman, R. C. Aalberse, J. Schuurman, J. G. van de Winkel, P. W. Parren, Therapeutic IgG4 antibodies engage in Fab-arm exchange with endogenous human IgG4 in vivo, Nat Biotechnol, 27 (2009) 767-771.
[17] J. Fu, J. Bongers, L. Tao, D. Huang, R. Ludwig, Y. Huang, Y. Qian, J. Basch, J. Goldstein, R. Krishnan, L. You, Z. J. Li, R. J. Russell, Characterization and identification of alanine to serine sequence variants in an IgG4 monoclonal antibody produced in mammalian cell lines, J Chromatogr B Analyt Technol Biomed Life Sci, 908 (2012) 1-8.
[18] H. Luo, M. Cao, K. Newell, C. Afdahl, J. Wang, W. K. Wang, Y. Li, Double-peak elution profile of a monoclonal antibody in cation exchange chromatography is caused by histidine-protonation-based charge variants, J Chromatogr A, 1424 (2015) 92-101.
[19] J. Guo, A. D. Creasy, G. Barker, G. Carta, Surface induced three-peak elution behavior of a monoclonal antibody during cation exchange chromatography, J Chromatogr A, 1474 (2016) 85-94.

```
SEQUENCE LISTING anti-CD137 antibody wild-type heavy chain sequence (SEQ ID NO: 1):
QVQLQQWGAGLLKPSETLSLTCAVYGGSFSGYYWSWIRQSPEKGLEWIGE
INHGGYVTYNPSLESRVTISVDTSKNQFSLKLSSVTAADTAVYYCARDYG
PGNYDWYFDLWGRGTLVTVSSASTKGPSVFPLAPCSRSTSESTAALGCLV
KDYFPEPVTVSWNSGALTSGVHTFPAVLQSSGLYSLSSVVTVPSSSLGTK
TYTCNVDHKPSNTKVDKRVESKYGPPCPSCPAPEFLGGPSVFLFPPKPKD
TLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK anti-CD137 wild-type light chain sequence (SEQ ID NO: 2):
EIVLTQSPATLSLSPGERATLSCRASQSVSSYLAWYQQKPGQAPRLLIYDASNRA
TGIPARFSGSGSGTDFTLTISSLEPEDFAVYYCQQRSNWPPALTFGGGTKVEIKRTVAA
PSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC
```

SEQUENCE LISTING mAb1 partial sequence (SEQ ID NO: 3):
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCP mAb2 partial sequence (SEQ ID NO: 4):
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCP mAb3 partial sequence (SEQ ID NO: 5):
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCP mAb4 partial sequence (SEQ ID NO: 6):
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCP mAb5 partial sequence (SEQ ID NO: 7):
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCP mAb6 partial sequence (SEQ ID NO: 8):
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCP mAb7 partial sequence (SEQ ID NO: 9):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP mAb8 partial sequence (SEQ ID NO: 10):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP mAb9 partial sequence (SEQ ID NO: 11):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP mAb10 partial sequence (SEQ ID NO: 12):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP mAb11 partial sequence (SEQ ID NO: 13):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP mAb12 partial sequence (SEQ ID NO: 14):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP mAb7-w partial sequence (SEQ ID NO: 15):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPSCP mAb12-w partial sequence (SEQ ID NO: 16):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPSCP mAb12-1 partial sequence (SEQ ID NO: 17):
ASTKGPSVFPLAPCSKSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCP mAb12-2 partial sequence (SEQ ID NO: 18):
ASTKGPSVFPLAPCSRSTSGSTAALGCLVKDYFPEPVTVSWNSGALTSGVHTFPAVLQSS
GLYSLSSVVTVPSSSLGTKTYTCNVDHKPSNTKVDKRVESKYGPPCPPCP mAb12-3 partial sequence (SEQ ID NO: 19):
ASTKGPSVFPLAPCSRSTSEGTAALGCLVKDYFPEPVTVSWNSGALTSGVHTFPAVLQSS
GLYSLSSVVTVPSSSLGTKTYTCNVDHKPSNTKVDKRVESKYGPPCPPCP mAb12-4a partial sequence (SEQ ID NO: 20):
ASTKGPSVFPLAPCSRSTSESTAALGCLVKDYFPEPVTVSWNSGALTSGVHTFPAVLQSS
GLYSLSSVVTVPSSSLGTQTYTCNVDHKPSNTKVDKRVESKYGPPCPPCP mAb12-4b partial sequence (SEQ ID NO: 21):
ASTKGPSVFPLAPCSRSTSESTAALGCLVKDYFPEPVTVSWNSGALTSGVHTFPAVLQSS
GLYSLSSVVTVPSSSLGTRTYTCNVDHKPSNTKVDKRVESKYGPPCPPCP

SEQUENCE LISTING

```
mAb12-4c partial sequence (SEQ ID NO: 22):
ASTKGPSVFPLAPCSRSTSESTAALGCLVKDYFPEPVTVSWNSGALTSGVHTFPAVLQSS
GLYSLSSVVTVPSSSLGTPTYTCNVDHKPSNTKVDKRVESKYGPPCPPCP mAb12-5 partial sequence (SEQ ID NO: 23):
ASTKGPSVFPLAPCSRSTSESTAALGCLVKDYFPEPVTVSWNSGALTSGVHTFPAVLQSS
GLYSLSSVVTVPSSSLGTKTYICNVDHKPSNTKVDKRVESKYGPPCPPCP mAb12-6 partial sequence (SEQ ID NO: 24):
ASTKGPSVFPLAPCSRSTSESTAALGCLVKDYFPEPVTVSWNSGALTSGVHTFPAVLQSS
GLYSLSSVVTVPSSSLGTKTYTCNVNHKPSNTKVDKRVESKYGPPCPPCP mAb12-7 partial sequence (SEQ ID NO: 25):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVEPKYGPPCPPCP mAb12-8 partial sequence (SEQ ID NO: 26):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKKGPPCPPCP mAb12-9 partial sequence (SEQ ID NO: 27):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYTPPCPPCP mAb12-10 partial sequence (SEQ ID NO: 28):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGHPCPPCP mAb12-11 partial sequence (SEQ ID NO: 29):
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPTCPPCP
```

We claim:

1. An IgG4 antibody comprising a heavy chain and a light chain, wherein the heavy chain comprises an amino acid sequence selected from SEQ ID NO: 22, 25, 27, 28 or 29.

2. The IgG4 antibody of claim 1, which is humanized or human.

3. The IgG4 antibody of claim 1, which is a full-length antibody.

4. The IgG4 antibody of claim 1, which is an antibody fragment.

5. The IgG4 antibody of claim 4, wherein the antibody fragment is a F(ab)$_2$.

6. The IgG4 antibody of claim 1, which binds to a target molecule selected from CD137, CXCR4, eTau, CSF1R, Lag3, PD1, PDL1 or KIR.

7. A fusion protein comprising an amino acid sequence selected from SEQ ID NO: 22, 25, 27, 28 or 29.

8. A pharmaceutical composition comprising (1) the IgG4 antibody of claim 1 or the fusion protein of claims 7; and (2) a pharmaceutically acceptable carrier.

9. A nucleic acid comprising a nucleotide sequence encoding the IgG4 antibody of claim 1 or the fusion protein of claim 7.

10. A vector comprising a nucleotide acid encoding the IgG4 antibody of claim 1 or the fusion protein of claim 7.

11. A host cell comprising a nucleotide acid encoding the IgG4 antibody of claim 1 or the fusion protein of claim 7.

12. A method of producing an IgG4 antibody or fusion protein, said method comprising culturing the host cell of claim 11 under conditions appropriate for the expression of the IgG4 antibody or the fusion protein.

* * * * *